US011998730B2

(12) United States Patent
Dague et al.

(10) Patent No.: US 11,998,730 B2
(45) Date of Patent: *Jun. 4, 2024

(54) ADAPTIVE SPEED CONTROL ALGORITHMS AND CONTROLLERS FOR OPTIMIZING FLOW IN VENTRICULAR ASSIST DEVICES

(71) Applicant: TC1 LLC, St. Paul, MN (US)

(72) Inventors: Charles Dague, Windham, NH (US); Dan Harjes, Carlisle, MA (US)

(73) Assignee: TC1 LLC, St. Paul, MN (US)

( * ) Notice: Subject to any disclaimer, the term of this patent is extended or adjusted under 35 U.S.C. 154(b) by 2 days.

This patent is subject to a terminal disclaimer.

(21) Appl. No.: 17/585,295

(22) Filed: Jan. 26, 2022

(65) Prior Publication Data

US 2022/0143385 A1     May 12, 2022

Related U.S. Application Data

(63) Continuation of application No. 16/552,102, filed on Aug. 27, 2019, now Pat. No. 11,241,572.

(Continued)

(51) Int. Cl.
*A61M 60/562* (2021.01)
*A61M 60/178* (2021.01)
(Continued)

(52) U.S. Cl.
CPC ........ *A61M 60/562* (2021.01); *A61M 60/178* (2021.01); *A61M 60/232* (2021.01);
(Continued)

(58) Field of Classification Search
CPC .............. A61M 60/562; A61M 60/178; A61M 60/232; A61M 60/237; A61M 60/422;
(Continued)

(56) References Cited

U.S. PATENT DOCUMENTS 3,985,123 A     10/1976  Herzlinger et al.
4,382,199 A      5/1983  Isaacson
(Continued)

FOREIGN PATENT DOCUMENTS

CN     103957959 A     7/2014
CN     107073183 A     8/2017
(Continued)

OTHER PUBLICATIONS

Antaki et al., "In Search of Chronic Speed Control for Rotary Blood Pumps", Proceedings of the Waseda International Congress of Modeling and Simulation Technology for Artificial Organs, Aug. 1-3, 1996, 2 pages.

(Continued)

*Primary Examiner* — Amanda K Hulbert
*Assistant Examiner* — Natasha Patel
(74) *Attorney, Agent, or Firm* — Kilpatrick Townsend & Stockton LLP

(57) ABSTRACT

Method and systems control a rotational speed of a blood pump during ventricular diastole. A method includes controlling a blood pump in accordance with a first segment operational mode. A controller monitors the blood flow rate through the blood pump. The controller determines, based on the blood flow rate, whether continued controlling of the blood pump per the first segment operational mode would result in the blood flow rate through the blood pump being less than a target minimum blood flow rate. In response to a determination that continued controlling of the blood pump per the first segment operational mode would result in the blood flow rate through the blood pump being less than the target minimum blood flow rate, the controller controls the rotational speed of the blood pump so that the blood flow rate through the blood pump is approximate to the target minimum blood flow rate.

20 Claims, 11 Drawing Sheets

Related U.S. Application Data

(60) Provisional application No. 62/736,013, filed on Sep. 25, 2018.

(51) Int. Cl.
*A61M 60/232* (2021.01)
*A61M 60/237* (2021.01)
*A61M 60/422* (2021.01)
*A61M 60/515* (2021.01)
*A61M 60/523* (2021.01)
*A61M 60/538* (2021.01)
*A61M 60/816* (2021.01)

(52) U.S. Cl.
CPC ........ *A61M 60/237* (2021.01); *A61M 60/422* (2021.01); *A61M 60/515* (2021.01); *A61M 60/523* (2021.01); *A61M 60/538* (2021.01); *A61M 60/816* (2021.01); *A61M 2205/3334* (2013.01); *A61M 2205/3365* (2013.01); *A61M 2230/06* (2013.01)

(58) Field of Classification Search
CPC .............. A61M 60/515; A61M 60/523; A61M 60/538; A61M 60/816; A61M 2205/3334; A61M 2205/3365; A61M 2230/06
See application file for complete search history.

(56) References Cited

U.S. PATENT DOCUMENTS

| | | | |
|---|---|---|---|
| 4,809,681 | A | 3/1989 | Kantrowitz et al. |
| 5,385,581 | A | 1/1995 | Bramm et al. |
| 5,693,091 | A | 12/1997 | Larson et al. |
| 5,695,471 | A | 12/1997 | Wampler |
| 5,697,884 | A | 12/1997 | Francischelli et al. |
| 5,708,346 | A | 1/1998 | Schob |
| 5,722,930 | A | 3/1998 | Larson, Jr. et al. |
| 5,807,234 | A | 9/1998 | Bui et al. |
| 5,833,619 | A | 11/1998 | Freed et al. |
| 5,888,242 | A | 3/1999 | Antaki et al. |
| 6,053,705 | A | 4/2000 | Schob et al. |
| 6,066,086 | A | 5/2000 | Antaki et al. |
| 6,071,093 | A | 6/2000 | Hart |
| 6,080,133 | A | 6/2000 | Wampler |
| 6,100,618 | A | 8/2000 | Schoeb et al. |
| 6,116,862 | A | 9/2000 | Rau et al. |
| 6,183,412 | B1 | 2/2001 | Benkowski et al. |
| 6,186,665 | B1 | 2/2001 | Maher et al. |
| 6,201,329 | B1 | 3/2001 | Chen |
| 6,222,290 | B1 | 4/2001 | Schob et al. |
| 6,234,772 | B1 | 5/2001 | Wampler et al. |
| 6,244,835 | B1 | 6/2001 | Antaki et al. |
| 6,249,067 | B1 | 6/2001 | Schob et al. |
| 6,264,635 | B1 | 7/2001 | Wampler et al. |
| 6,278,251 | B1 | 8/2001 | Schoeb |
| 6,342,071 | B1 | 1/2002 | Pless et al. |
| 6,344,022 | B1 | 2/2002 | Jarvik et al. |
| 6,351,048 | B1 | 2/2002 | Schob et al. |
| 6,355,998 | B1 | 3/2002 | Schob et al. |
| 6,572,530 | B1 | 6/2003 | Araki et al. |
| 6,634,224 | B1 | 10/2003 | Schoeb et al. |
| 6,688,861 | B2 | 2/2004 | Wampler |
| 6,879,074 | B2 | 4/2005 | Amrhein et al. |
| 6,991,595 | B2 | 1/2006 | Burke et al. |
| 7,112,903 | B1 | 9/2006 | Schob |
| 7,238,165 | B2 | 7/2007 | Vincent et al. |
| 7,699,586 | B2 | 4/2010 | LaRose et al. |
| 7,976,271 | B2 | 7/2011 | LaRose et al. |
| 7,997,854 | B2 | 8/2011 | LaRose et al. |
| 8,007,254 | B2 | 8/2011 | LaRose et al. |
| 8,152,493 | B2 | 4/2012 | LaRose et al. |
| 8,323,174 | B2 | 12/2012 | Jeevanandam et al. |
| 8,419,609 | B2 | 4/2013 | Shambaugh, Jr. et al. |
| 8,449,444 | B2 | 5/2013 | Poirier |
| 8,506,471 | B2 | 8/2013 | Bourque |
| 8,562,508 | B2 | 10/2013 | Dague et al. |
| 8,597,350 | B2 | 12/2013 | Rudser et al. |
| 8,652,024 | B1 | 2/2014 | Yanai et al. |
| 8,657,733 | B2 | 2/2014 | Ayre et al. |
| 8,668,473 | B2 | 3/2014 | LaRose et al. |
| 8,852,072 | B2 | 10/2014 | LaRose et al. |
| 8,864,643 | B2 | 10/2014 | Reichenbach et al. |
| 8,882,744 | B2 | 11/2014 | Dormanen et al. |
| 9,068,572 | B2 | 6/2015 | Ozaki et al. |
| 9,079,043 | B2 | 7/2015 | Stark et al. |
| 9,091,271 | B2 | 7/2015 | Bourque |
| 9,265,870 | B2 | 2/2016 | Reichenbach et al. |
| 9,382,908 | B2 | 7/2016 | Ozaki et al. |
| 9,901,666 | B2 | 2/2018 | Cotter |
| 2001/0021817 | A1 | 9/2001 | Brugger et al. |
| 2003/0199727 | A1* | 10/2003 | Burke ................. A61M 60/216 600/16 |
| 2004/0152944 | A1* | 8/2004 | Medvedev .......... A61M 60/546 600/17 |
| 2005/0071001 | A1 | 3/2005 | Jarvik |
| 2005/0131271 | A1 | 6/2005 | Benkowski et al. |
| 2012/0088955 | A1 | 4/2012 | Taub et al. |
| 2013/0314047 | A1 | 11/2013 | Eagle et al. |
| 2014/0100413 | A1* | 4/2014 | Casas ................. A61M 60/546 600/16 |
| 2014/0200390 | A1 | 7/2014 | Yanai et al. |
| 2015/0051437 | A1 | 2/2015 | Miyakoshi et al. |
| 2015/0151032 | A1 | 6/2015 | Voskoboynikov et al. |
| 2015/0290374 | A1 | 10/2015 | Bourque et al. |
| 2017/0049945 | A1* | 2/2017 | Halvorsen .......... A61M 60/216 |
| 2017/0239407 | A1* | 8/2017 | Hayward ............ A61M 60/523 |
| 2019/0209755 | A1* | 7/2019 | Nix ..................... A61M 60/178 |

FOREIGN PATENT DOCUMENTS

| | | |
|---|---|---|
| EP | 654276 | 5/1995 |
| EP | 877633 | 7/2005 |
| EP | 1354606 | 6/2006 |
| EP | 1812094 | 8/2007 |
| WO | 9819624 | 5/1998 |
| WO | 0172352 | 10/2001 |
| WO | 2006055745 | 8/2006 |

OTHER PUBLICATIONS

Antaki et al., "In Vivo Evaluation of the Nimbus Axial Flow Ventricular Assist System Criteria and Methods", ASAIO Journal, vol. 39, No. 3, Jul.-Sep. 1993, pp. M231-M236.

Mitamura et al., "Development of an Implantable Motor-Driven Assist Pump System", IEEE Transactions on Biomedical Engineering, vol. 37, No. 2, Feb. 1, 1990, pp. 146-156.

\* cited by examiner

Flow (Q)
Typical Head/Flow Curve for centrifugal LVAD

ADAPTIVE SPEED CONTROL ALGORITHMS AND CONTROLLERS FOR OPTIMIZING FLOW IN VENTRICULAR ASSIST DEVICES

CROSS REFERENCE TO RELATED APPLICATION DATA

The present application is a Continuation of U.S. patent application Ser. No. 16/552,102 filed Aug. 27, 2019 (now U.S. Pat. No. 11,241,572); which claims the benefit of U.S. Provisional Appln. No. 62/736,013 filed Sep. 25, 2018; the full disclosures which are incorporated herein by reference in their entirety for all purposes.

BACKGROUND

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave a heart too weak to pump enough blood to the body. As symptoms worsen, advanced heart failure develops.

A patient suffering from heart failure, also called congestive heart failure, may use a VAD while awaiting a heart transplant or as a long term destination therapy. In another example, a patient may use a VAD while their own native heart recovers. Thus, a VAD can supplement a weak heart (i.e., partial support) or can effectively replace the natural heart's function. VADs can be implanted in the patient's body and powered by an electrical power source inside or outside the patient's body.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Methods for controlling a rotational speed of a continuous flow blood pump, and related mechanical circulatory assist systems, modulate the rotational speed of the blood pump based on pump blood flow rate to prevent the flow rate through the blood pump from dropping below a target minimum blood flow rate during ventricular diastole. The flow rate through a continuous flow blood pump, such as a centrifugal blood pump or an axial flow blood pump, for a given rotational speed of the blood pump, decreases in response to an increase in the pressure differential across the blood pump. For a left ventricular assist device, the pressure differential across the blood pump is substantially equal to the pressure differential between the left ventricular pressure and the aortic pressure. For a right ventricular assist device, the pressure differential across the blood pump is substantially equal to the pressure differential between the right ventricular pressure and the pulmonary artery pressure. During ventricular diastole, the pressure within the ventricle decreases, thereby increasing the pressure differential across the blood pump and causing the flow rate through the blood pump to decrease. In some instances, a patient's systemic blood pressure can change over time so that the pressure differential across the blood pump during ventricular diastole is substantially higher, thereby substantially decreasing the flow rate through the blood pump during ventricular diastole. By modulating the rotation speed of the blood pump based on pump blood flow rate, the flow rate through the blood pump can be prevented from dropping below a target minimum blood flow rate over a suitable range of variation in patient blood pressure.

Thus, in one aspect, a method of controlling a rotational speed of a continuous flow blood pump of a ventricular assist device to control a rate of flow of blood through the blood pump during ventricular diastole includes pumping, via the ventricular assist device, blood from a ventricle of a patient to an artery of the patient over a first segment of a cardiac cycle of the patient. The rotation rate of the blood pump over the first segment is controlled, by a controller, in accordance with a first segment operational mode for the blood pump. The blood flow rate through the blood pump is monitored by the controller. The controller determines, based on the blood flow rate through the blood pump, whether continued controlling of the rotation rate of the blood pump over a second segment of the cardiac cycle in accordance with the first segment operational mode would result in the blood flow rate through the blood pump being less than a target minimum blood flow rate. In response to the determination that continued controlling of the rotation rate of the blood pump over the second segment in accordance with the first segment operational mode would result in the blood flow rate through the blood pump being less than the target minimum blood flow rate, the controller controls the rotational speed of the blood pump over the second segment so that the blood flow rate through the blood pump is approximate to the target minimum blood flow rate.

Any suitable controller can be used in the method to control the rotational speed of the continuous flow blood pump during ventricular diastole. For example, in some embodiments, the controller includes a speed controller integral to the blood pump. In other embodiments, the controller is disposed in a separately implantable unit or is disposed in a non-implanted external control unit.

In the method to control the rotational speed of the continuous flow blood pump during ventricular diastole, the controller can monitor the blood flow rate through the blood pump using any suitable approach. For example, in some embodiments, the controller can monitor the blood flow rate through the blood pump via pump electronics, which can be integral to the blood pump, disposed in a separately implantable unit, and/or is disposed in a non-implanted external control unit.

In many embodiments of the method, the target minimum blood flow rate can be any suitable blood flow rate through the blood pump during ventricular diastole for the patient. For example, in many embodiments of the method, the target minimum blood flow rate is within a range from approximately 0.0 liters/minute to 2.0 liters/minute. In some embodiments of the method, the target minimum blood flow rate is within a range from 0.5 liters/minute to 1.5 liters/minute. In some embodiments of the method, the target minimum blood flow rate is within a range from 0.8 liters/minute to 1.2 liters/minute. For another embodiment, the blood pump is controlled to act as a one-way valve in diastole, with a net diastolic blood flow at or close to 0.0 liters/minute.

In many embodiments of the method, the controller compares the current blood flow rate through the blood pump to the target minimum blood flow rate to determine whether to continue to control operation of the blood pump per the first segment operational mode or to switch to controlling the rotation rate of the blood pump to pump blood through the blood pump at the target minimum blood flow rate. For example, in some embodiments of the method, the determination of whether continued controlling of the rotation rate of the blood pump over the second segment of the cardiac cycle in accordance with the first segment operational mode would result in the blood flow rate through the blood pump being less than the target minimum blood flow rate includes determining a relative difference between a current blood flow rate through the blood pump and the target minimum blood flow rate. In some embodiments of the method, the determination of whether continued controlling of the rotation rate of the blood pump over the second segment of the cardiac cycle in accordance with the first segment operational mode would result in the blood flow rate through the blood pump being less than the target minimum blood flow rate further includes determining a current rate of change in the blood flow rate through the blood pump.

The method can be practiced in conjunction with any suitable first segment operational mode of the blood pump. For example, in some embodiments of the method, the rotation rate of the blood pump in the first segment operational mode is constant. In some embodiments of the method, the rotation rate of the blood pump in the first segment operational mode is varied to generate a periodic pulsatile blood flow. In some embodiments of the method, the periodic pulsatile blood flow is synchronized with the cardiac cycle of the patient. In some embodiments of the method, the periodic pulsatile blood flow is synchronized with the cardiac cycle of the patient based on the monitored blood flow through the blood pump. In some embodiments of the method, the rotation rate of the blood pump over the first segment is controlled, by the controller, to generate a blood pressure pulse during ventricular systole.

In many embodiments, the method further includes switching back to controlling operation of the blood pump in accordance with the first segment operational mode at a suitable point in the cardiac cycle. For example, in many embodiments of the method, the controller detects an end of the second segment by detecting when the rotation rate of the blood pump for pumping blood at the target minimum blood flow rate decreases to or below the rotation rate of the blood pump in accordance with the first segment operational mode for the blood pump. In response to detecting the end of the second segment, the controller switches back to controlling the rotation rate in accordance with the first segment operational mode for the blood pump.

In many embodiments of the method, the first segment operational mode provides a level of circulatory support during ventricular systole suitable for exercising a semilunar valve of the patient and/or for attempting to wean the patient off of the ventricular assist device. Accordingly, in many embodiments of the method, the rotation rate of the blood pump in the first segment operational mode results in an opening and a closing of a semilunar valve of the patient during ventricular systole. When attempting to wean the patient off of the ventricular assist device, the target minimum blood flow rate can be selected to prevent the occurrence of a substantial rate of retrograde flow through the blood pump. For example, the target minimum blood flow rate can be within a range from about 0.0 liters/minute to 0.5 liters/minute when attempting to wean the patient off of the ventricular assist device. In some embodiments of the method, the target minimum blood flow rate can be 0.0 liters/minute when attempting to wean the patient off of the ventricular assist device.

Any suitable approach can be used by the controller to monitor the blood flow rate through the blood pump. For example, in some embodiments of the method, the monitoring of the blood flow rate through the blood pump by the controller includes estimating the blood flow rate based on the rate of rotation of the blood pump and an operational parameter indicative of power consumption by the blood pump. In some embodiments of the method, the monitoring of the blood flow rate through the blood pump by the controller includes estimating the blood flow rate based on the rate of rotation of the blood pump and an operational parameter indicative of a pressure differential across the blood pump.

In some embodiments of the method, the controller updates the target minimum blood flow rate based on patient activity level. For example, in some embodiments, the method includes measuring, via a sensor, a patient physiological parameter indicative of an activity level of the patient. In some embodiments, the controller updates the target minimum blood flow rate based on the patient physiological parameter.

In many embodiments of the method, the rotation rate of the blood pump over the first segment can be selectively switched between being controlled, by the controller, in accordance with the first segment operational mode to being controlled via the second segment operational mode, and vice-versa. Any suitable criteria and/or clinician input can be used to select when the rotation rate of the blood pump over the first segment is controlled via the first segment operational mode or the second segment operational mode.

In another aspect, a mechanical circulatory assist system includes a continuous flow blood pump and a controller. The continuous flow blood pump is implantable in fluid communication with a ventricle and an artery of a patient to assist blood flow from the ventricle to the artery. The controller is operatively connected to the blood pump. The controller is operable to control a rotation speed of the blood pump to pump blood from the ventricle to the artery. The rotation rate of the blood pump over a first segment is controlled in accordance with a first segment operational mode for the blood pump. The controller is operable to monitor the blood flow rate through the blood pump. Based on the monitored blood flow rate through the blood pump, the controller determines whether continuing to control the rotation rate of the blood pump over a second segment of the cardiac cycle in accordance with the first segment operational mode would result in the blood flow rate through the blood pump being less than a target minimum blood flow rate. In response to determining that continuing to control the rotation rate of the blood pump over the second segment in accordance with the first segment operational mode would result in the blood flow rate through the blood pump being less than the target minimum blood flow rate, the controller controls the rotational speed of the blood pump over the second segment so that the blood flow rate through the blood pump is approximate to the target minimum blood flow rate.

In many embodiments of the system, the target minimum blood flow rate can be any suitable blood flow rate through the blood pump during ventricular diastole for the patient.

For example, in many embodiments of the system, the target minimum blood flow rate is within a range from about 0 liters/minute to 2.0 liters/minute. In some embodiments of the system, the target minimum blood flow rate is within a range from 0.5 liters/minute to 1.5 liters/minute. In some embodiments of the system, the target minimum blood flow rate is within a range from 0.8 liters/minute to 1.2 liters/minute. For another embodiment, the blood pump is controlled to act as a one-way valve in diastole, with a net diastolic blood flow at or close to 0.0 liters/minute.

In many embodiments of the system, the controller compares the current blood flow rate through the blood pump to the target minimum blood flow rate to determine whether to continue to control operation of the blood pump per the first segment operational mode or to switch to controlling the rotation rate of the blood pump to pump blood through the blood pump at the target minimum blood flow rate. For example, in some embodiments of the system, the determination of whether continued controlling of the rotation rate of the blood pump over the second segment of the cardiac cycle in accordance with the first segment operational mode would result in the blood flow rate through the blood pump being less than the target minimum blood flow rate includes determining a relative difference between a current blood flow rate through the blood pump and the target minimum blood flow rate. In some embodiments of the system, the determination of whether continued controlling of the rotation rate of the blood pump over the second segment of the cardiac cycle in accordance with the first segment operational mode would result in the blood flow rate through the blood pump being less than the target minimum blood flow rate further includes determining a rate of change in the blood flow rate through the blood pump.

In many embodiments of the system, any suitable first segment operational mode of the blood pump can be used. For example, in some embodiments of the system, the rotation rate of the blood pump in the first segment operational mode is constant. In some embodiments of the system, the rotation rate of the blood pump in the first segment operational mode is varied to generate a periodic pulsatile blood flow. In some embodiments of the system, the periodic pulsatile blood flow is synchronized with the cardiac cycle of the patient. In some embodiments of the system, the periodic pulsatile blood flow is synchronized with the cardiac cycle of the patient based on the monitored blood flow through the blood pump. In some embodiments of the system, the rotation rate of the blood pump over the first segment is controlled, by the controller, to generate a blood pressure pulse during ventricular systole.

In many embodiments of the system, the controller switches back to controlling operation of the blood pump in accordance with the first segment operational mode at a suitable point in the cardiac cycle. For example, in many embodiments of the system, the controller detects an end of the second segment by detecting when the rotation rate of the blood pump for pumping blood at the target minimum blood flow rate decreases to or below the rotation rate of the blood pump in accordance with the first segment operational mode for the blood pump. In response to detecting the end of the second segment, the controller switches back to controlling the rotation rate in accordance with the first segment operational mode for the blood pump.

In many embodiments of the system, the first segment operational mode provides a level of circulatory support during ventricular systole suitable for exercising a semilunar valve of the patient and/or for attempting to wean the patient off of the ventricular assist device. Accordingly, in many embodiments of the system, the rotation rate of the blood pump in the first segment operational mode results in an opening and a closing of a semilunar valve of the patient during ventricular systole. When attempting to wean the patient off of the ventricular assist device, the target minimum blood flow rate can be selected to prevent the occurrence of a substantial rate of retrograde flow through the blood pump. For example, the target blood flow rate can be within a range from about 0.0 liters/minute to 0.5 liters/minute when attemping to wean the patient off of the ventricular assist device. In some embodiments of the system, the target minimum blood flow rate can be 0.0 liters/minute when attempting to wean the patient off of the ventricular assist device.

In many embodiments of the system, a suitable approach can be used by the controller to monitor the blood flow rate through the blood pump. For example, in some embodiments of the system, the controller estimates the blood flow rate based on the rate of rotation of the blood pump and an operational parameter indicative of power consumption by the blood pump. In some embodiments of the system, the controller estimates the blood flow rate based on the rate of rotation of the blood pump and an operational parameter indicative of a pressure differential across the blood pump.

In some embodiments of the system, the controller updates the target minimum blood flow rate based on patient activity level. For example, in some embodiments, the system includes a sensor that measures a patient physiological parameter indicative of an activity level of the patient. In some embodiments of the system, the controller updates the target minimum blood flow rate based on the patient physiological parameter. In some embodiments of the system, the sensor includes a heart rate sensor. In some embodiments of the system, the sensor includes an accelerometer.

For a fuller understanding of the nature and advantages of the present invention, reference should be made to the ensuing detailed description and accompanying drawings.

DETAILED DESCRIPTION

Figure 1:
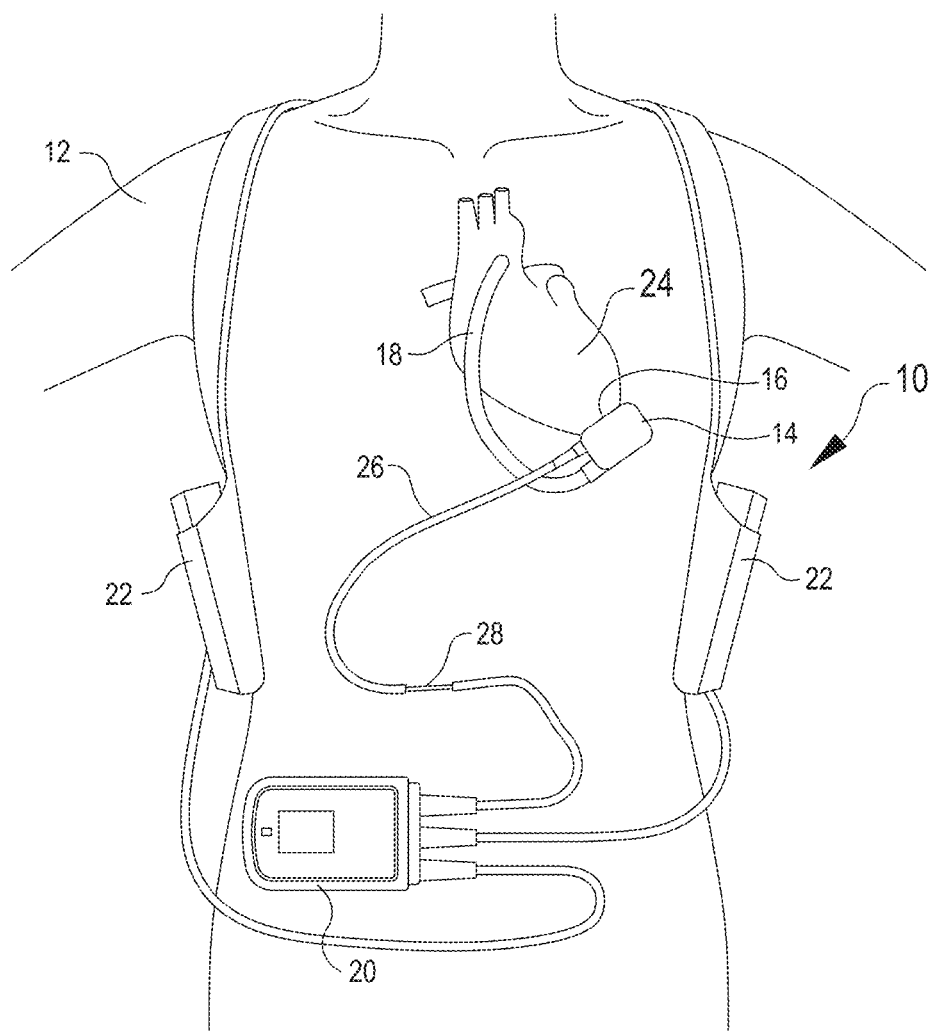
FIG. 1 is an illustration of a mechanical circulatory support system that includes a ventricular assist device (VAD) implanted in a patient's body, in accordance with many embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Methods for controlling a rotational speed of a blood pump, and related mechanical circulatory assist systems, modulate the rotational speed of the blood pump, during ventricular diastole, based on pump blood flow rate to prevent the flow rate through the blood pump from dropping below a target minimum blood flow rate. With continuous flow blood pumps, such as employed in many ventricular assist devices (VADs), blood flow rate through the blood pump is dependent on the rotational speed of the blood pump and the pressure differential across the blood pump. For example, for a left ventricular assist device (LVAD), the pressure differential across the blood pump is approximately equal to the aortic pressure minus the left ventricular pressure. In many instances, a physician sets the rotational speed of the VAD using echocardiography and pump performance parameters such as the estimated flow. A single set-it-and-forget-it speed setting, however, may not be optimal for a patient once discharged, as volume status may change, the native heart may change shape, and physiologic pressures can change. The methods and systems described herein employ an adaptive approach in which the rotational speed of the blood pump is modulated to maintain an optimal diastolic flow.

The methods and systems described herein can be implemented in connection with any suitable continuous flow pump. For example, one particularly suitable type of blood pump includes a magnetically levitated rotor/impeller. In many instances, a blood pump that includes a magnetically levitated rotor/impeller is capable of the rotational speed modulation described herein, which may occur once every cardiac cycle during ventricular diastole. By modulating the rotational speed of the blood pump during ventricular diastole, the sensitivity of a continuous flow blood pump (e.g., a centrifugal LVAD) to changes in pressure differential across the blood pump can be reduced, thereby preventing unsuitably low blood flow rate through the blood pump during ventricular diastole.

With good flow rate estimation accuracy, the rotational speed of a blood pump can be modulated to maintain optimal or desired flow in ventricular diastole and/or ventricular systole. During ventricular diastole, the aortic valve closes and the pressure gradient across the blood pump is maximized. If the rotational speed of the blood pump is held constant, the blood flow rate through the blood pump will reach its minimum during ventricular diastole. A physician will typically set the rotational speed of the blood pump low enough to ensure that the blood flow rate through the blood pump is low enough to not induce a ventricular suction event. With the blood flow rate through the blood pump already being low enough to avoid a suction event, any subsequent increase in the patient's blood pressure would further reduce the blood flow rate through the blood pump during ventricular diastole. The methods and systems described herein modulate the rotational speed of the blood pump to ensure adequate unloading of the ventricle over wide variations in blood pressure.

The methods and systems described herein can be implemented in any suitable operational scenario. For example, the methods and systems described herein can be used during normal operational scenarios in order to increase the effectiveness of the blood pump. As another example, the methods and systems can be used in connection with attempts to wean a patient off of a VAD to enable device removal. In many instances, an attempt to wean a patient off of a VAD includes a temporary reduction in the rotational speed of the blood pump to temporarily increase the burden placed on the patient's native heart. The reduction in speed of the blood pump, however, can result, in many instances, in retrograde flow through the blood pump during ventricular diastole, which is not representative of having no device at all. Accordingly, the methods and systems described herein can be employed during an attempt to wean a patient from a VAD in which the rotational speed of the VAD is modulated so that blood flow rate through the blood pump during ventricular diastole is near zero (i.e. no diastolic offloading and no retrograde flow).

Mechanically Circulatory Assist Systems

Figure 2:
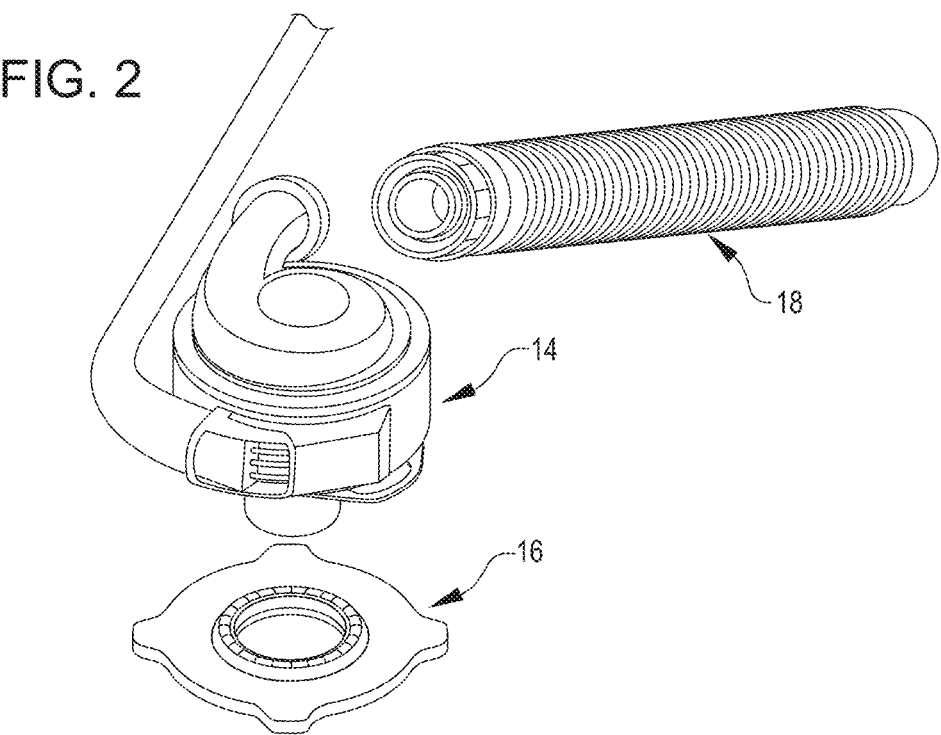
FIG. 2 is an exploded view of implanted components of the circulatory support system of FIG. 1.

Referring now to the drawings, in which like reference numerals represent like parts throughout the several views, FIG. 1 is an illustration of a mechanical circulatory support system 10 that includes a ventricular assist device (VAD) 14 implanted in a patient's body 12. The mechanical circulatory support system 10 includes the VAD 14, a ventricular cuff 16, an outflow cannula 18, an external system controller 20, and power sources 22. A VAD 14 can be attached to an apex of the left ventricle, as illustrated, or the right ventricle, or a separate VAD can be attached to each of the ventricles of the heart 24. The VAD 14 can be capable of pumping the entire flow of blood delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,419,609, 8,652,024, 8,668,473, 8,852,072, 8,864,643, 8,882,744, 9,068,572, 9,091,271, 9,265,870, and 9,382,908, all of which are incorporated herein by reference for all purposes in their entirety. With reference to FIG. 1 and FIG. 2, the VAD 14 can be attached to the heart 24 via the ventricular cuff 16, which can be sewn to the heart 24 and coupled to the VAD 14. In the illustrated embodiment, the output of the VAD 14 connects to the ascending aorta via the outflow cannula 18 so that the VAD 14 effectively diverts blood from the left ventricle and propels it to the aorta for circulation through the rest of the patient's vascular system.

FIG. 1 illustrates the mechanical circulatory support system 10 during battery 22 powered operation. A driveline 26 that exits through the patient's abdomen 28 connects the VAD 14 to the external system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system 10 can be powered by either one, two, or more batteries 22. It will be appreciated that although the system controller 20 and power source 22 are illustrated outside/external to the patient body 12, the driveline 26, the system controller 20 and/or the power source 22 can be partially or fully implantable within the patient 12, as separate components or integrated with the VAD 14. Examples of such modifications are further described in U.S. Pat. Nos. 8,562,508 and 9,079,043, all of which are incorporated herein by reference for all purposes in their entirety.

Figure 3:
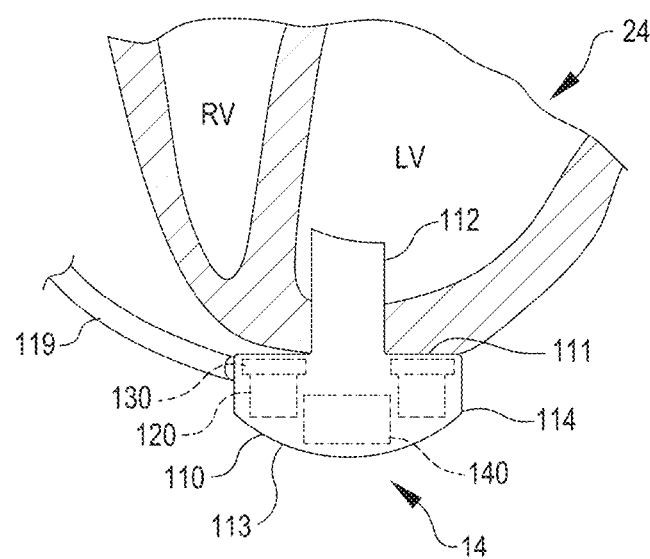
FIG. 3 is an illustration of the VAD of FIG. 1 attached to the patient's heart to augment blood pumping by the patient's left ventricle.
Figure 4:
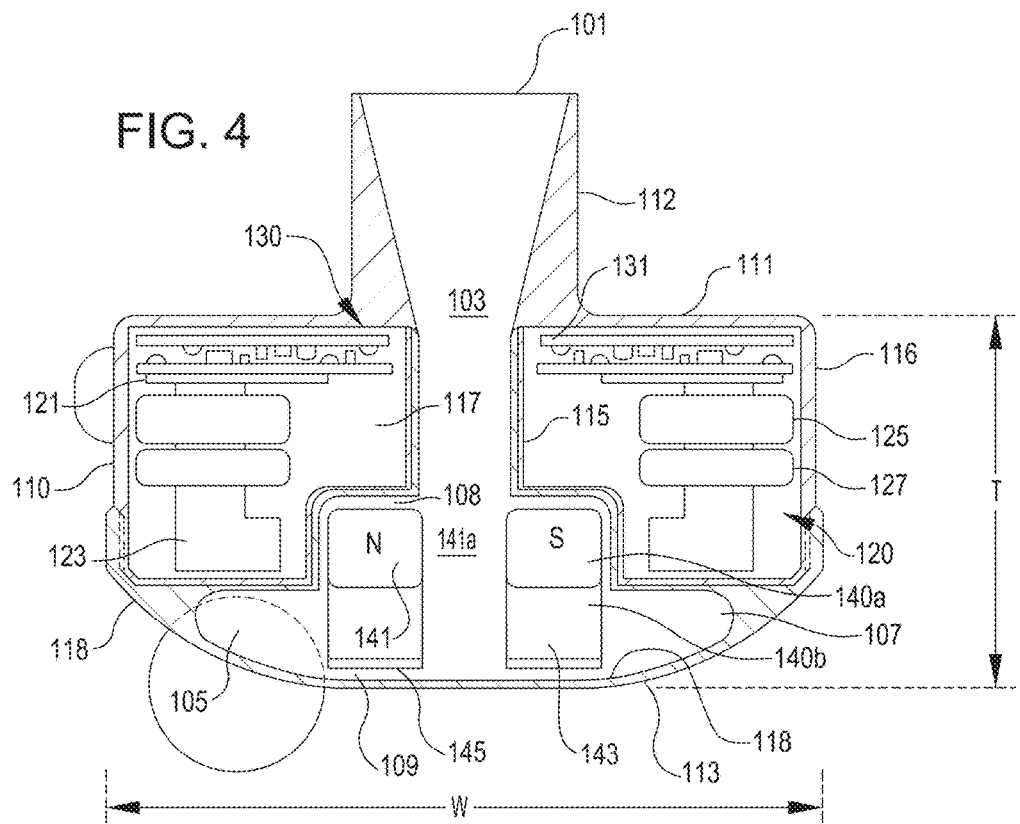
FIG. 4 is a cross-sectional view of the VAD of FIG. 3.

With reference to FIG. 3 and FIG. 4, the VAD 14 has a circular shaped housing 110 and is shown implanted within the patient 12 with a first face 111 of the housing 110 positioned against the patient's heart 24 and a second face 113 of the housing 110 facing away from the heart 24. The first face 111 of the housing 110 includes an inlet cannula 112 extending into the left ventricle LV of the heart 24. The second face 113 of the housing 110 has a chamfered edge 114 to avoid irritating other tissue that may come into contact with the VAD 14, such as the patient's diaphragm. To construct the illustrated shape of the puck-shaped housing 110 in a compact form, a stator 120 and electronics 130 of the VAD 14 are positioned on the inflow side of the housing toward first face 111, and a rotor 140 of the VAD 14 is positioned along the second face 113. This positioning of the stator 120, electronics 130, and rotor 140 permits the edge 114 to be chamfered along the contour of the rotor 140, as illustrated in at least FIG. 3 and FIG. 4, for example.

Referring to FIG. 4, the VAD 14 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the VAD 14 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIG. 4, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a can also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the VAD 14 can include one or more Hall sensors that may provide an output voltage, which is directly proportional to a strength of a magnetic field that is located in between at least one of the pole pieces 123a-123f and the permanent magnet 141, and the output voltage may provide feedback to the control electronics 130 of the VAD 14 to determine if the rotor 140 and/or the permanent magnet 141 is not at its intended position for the operation of the VAD 14. For example, a position of the rotor 140 and/or the permanent magnet 141 can be adjusted, e.g., the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 can be approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the VAD 14. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no magnetic-field generating rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the one or more Hall sensors may sense a current position of the rotor 140 and/or the permanent magnet 141, wherein the output voltage of the one or more Hall sensors may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into VAD 14 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 5:
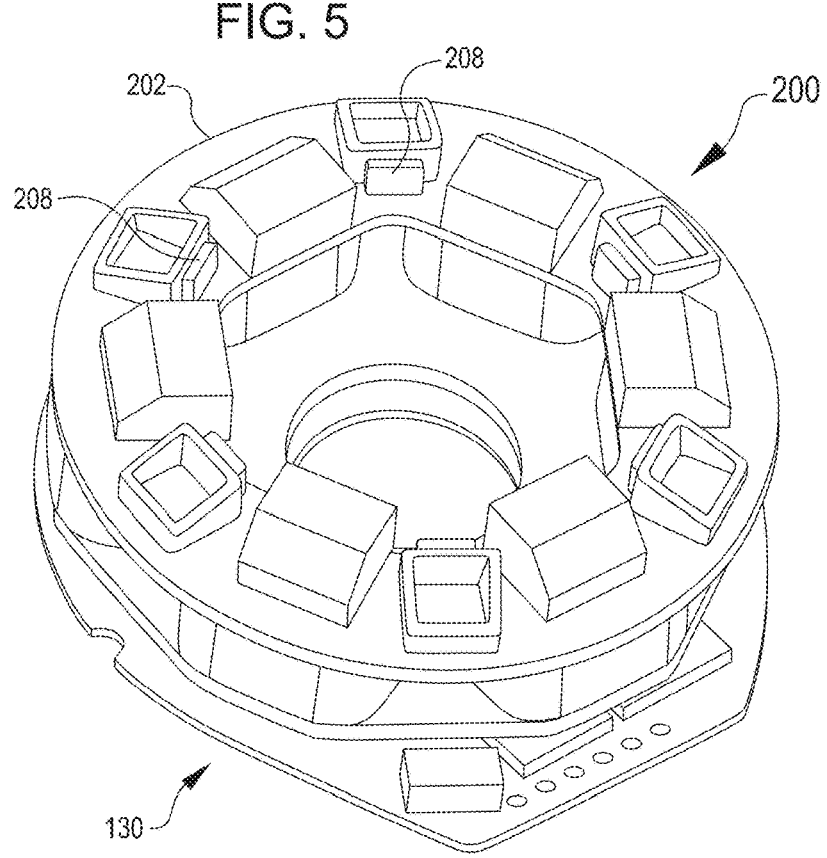
FIG. 5 is an illustration of an embodiment of a control unit for the VAD of FIG. 3.

FIG. 5 shows a Hall Sensor assembly 200 for the VAD 14, in accordance with many embodiments. The Hall Sensor assembly 200 includes a printed circuit board (PCB) 202 and six individual Hall Effect sensors 208 supported by the printed circuit board 202. The Hall Effect sensors 208 are configured to transduce a position of the rotor 140 of the VAD 14. In the illustrated embodiment, the Hall Effect sensors 208 are supported so as to be standing orthogonally relative to the PCB 202 and a longest edge of each of the Hall Effect sensors 208 is aligned to possess an orthogonal component with respect to the surface of the PCB 202. Each of the Hall Effect sensors 208 generates an output voltage, which is directly proportional to a strength of a magnetic field that is located in between at least one of the pole pieces 123a-123f and the permanent magnet 141. The voltage output by each of the Hall Effect sensors 208 is received by the control electronics 130, which processes the sensor output voltages to determine the position and orientation of the rotor 140. The determined position and orientation of the rotor 140 is used to determine if the rotor 140 is not at its intended position for the operation of the VAD 14. For example, a position of the rotor 140 and/or the permanent magnet 141 may be adjusted, for example, the rotor 140 or the permanent magnet 141 may be pushed or pulled towards a center of the blood flow conduit 103 or towards a center of the stator 120. The determined position of the rotor 140 can also be used to determine rotor eccentricity or a target rotor eccentricity, which can be used as described in U.S. Pat. No. 9,901,666, all of which is incorporated herein by reference for all purposes in its entirety, to estimate flow rate of blood pumped by the VAD 14.

Figure 6:
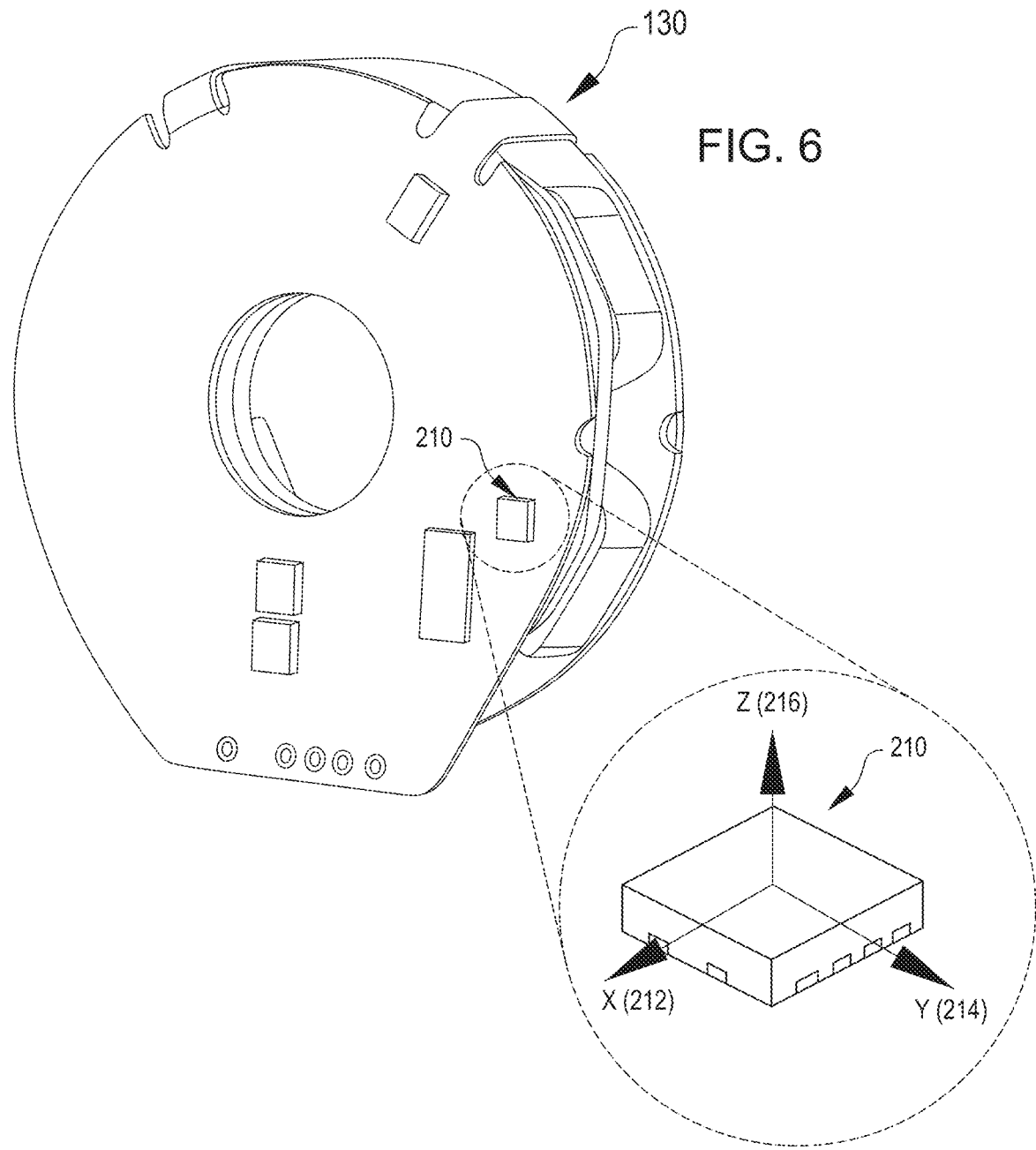
FIG. 6 is a heart-side view of the control unit of FIG. 5 showing a three-axis accelerometer included in the control unit, in accordance with many embodiments.

FIG. 6 is a heart-side view of the control electronics 130 showing an accelerometer 210 included in the control electronics 130, in accordance with many embodiments. In the many embodiments, the accelerometer 210 is a three-axis accelerometer that measures accelerations experienced by the control electronics 130 (and thereby the VAD 14) in three orthogonal axes (i.e., an X-axis 212, a Y-axis 214, and a Z-axis 216). In the illustrated embodiment, the X-axis 212 and the Y-axis 214 are each oriented orthogonal to an axis of rotation of the rotor 140, and the Z-axis 216 is parallel to the axis of rotation of the rotor 140.

Figure 7:
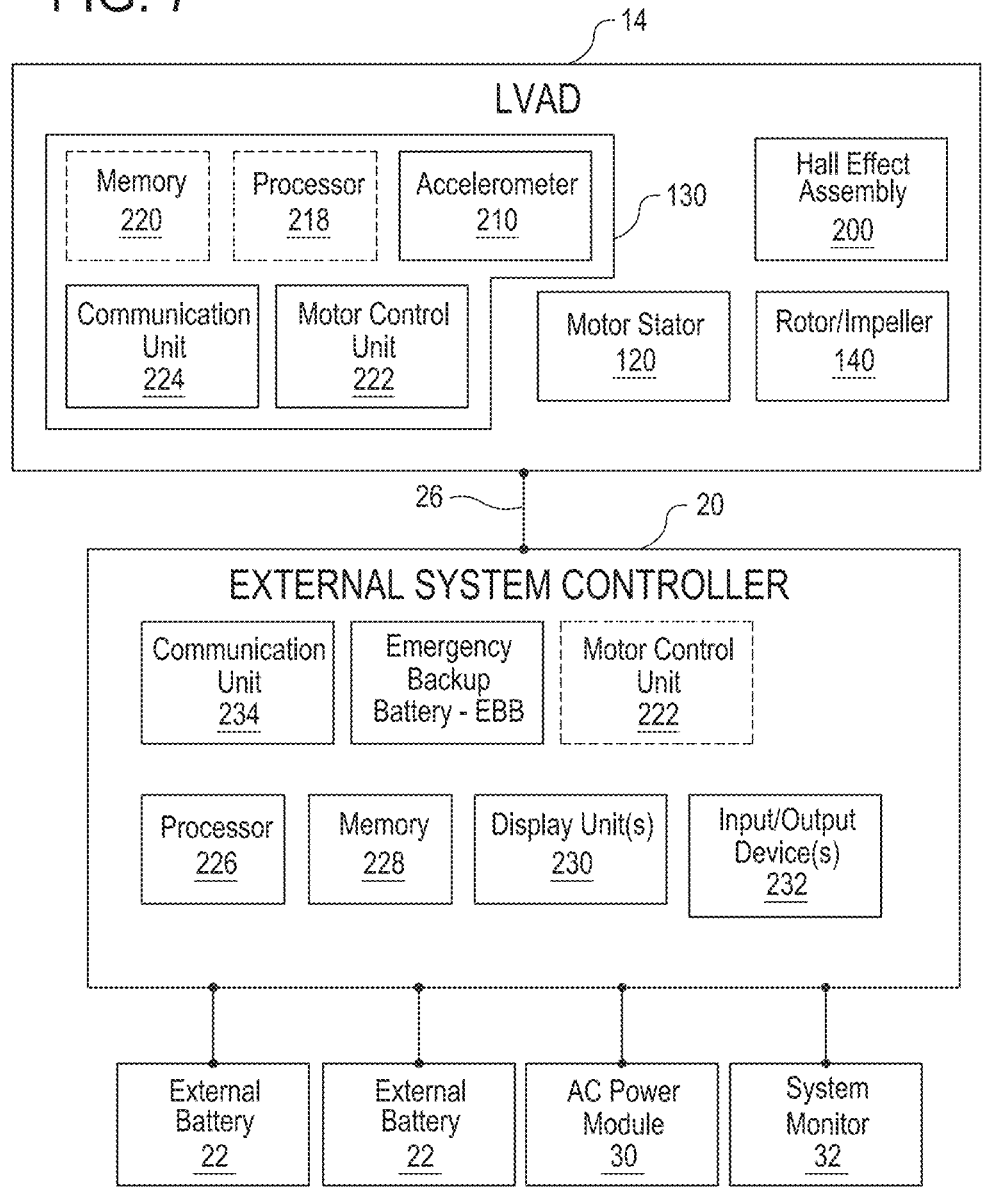
FIG. 7 is a schematic diagram of a control system architecture, in accordance with embodiments, of the mechanical support system of FIG. 1.

FIG. 7 is a schematic diagram of a control system architecture of the mechanical support system 10. The driveline 26 couples the implanted VAD 14 to the external system controller 20, which monitors system operation via various software applications.

The VAD 14 includes the control electronics 130, the Hall Effect Sensor assembly 200, the motor stator 120, the rotor/impeller 140. In the illustrated embodiment, the control electronics include a processor 218, a memory device 220 (which can include read-only memory and/or random access-memory), the accelerometer 210, a motor control unit 222, and a communication unit 224. In some embodiments, the memory device 220 stores one or more software applications that are executable by the processor 218 for various functions. For example, the one or more software applications can effectuate control the motor control unit 222 to effectuate radial levitation and rotational drive of the rotor 140 during operation. In some embodiments, the one or more programs effectuate processing of output from the accelerometer 210 and/or operational parameters for the VAD 14 (e.g., drive current, rotational speed, flow rate, pressure differential across the impeller) as described herein to detect and/or measure patient physiological events and/or activity (e.g., patient orientation, patient activity level, heart wall motion, heart sounds, heart rate, respiratory rate, diaphragm contraction, cardiac cycle timing). The one or more programs can effectuate control of the motor control unit 222 to synchronize variation in output of the VAD 14 with the patient's cardiac cycle timing as described herein. For example, the output of the VAD 14 can be increased over a period of time during ventricular systole so as to augment pumping of blood that occurs via contraction of the ventricle, thereby reducing the associated load on the ventricle. The one or more programs can effectuate control of the motor control unit 222 to vary output of the VAD 14 based on patient activity level. For example, in many embodiments, the output of the VAD 14 is increased in response to increased patient activity and decreased in response to decreased patient activity. The one or more programs can also be used to effectuate processing of the output from the accelerometer 210 and/or the operational parameters for the VAD 14 to generate patient monitoring data and/or VAD monitoring data as described herein. The communication unit 224 provides for wired and/or wireless communication between the VAD 14 and the external system controller 20. In some embodiments, the motor control unit 222 is included in the VAD 14. In other embodiments, the motor control unit 222 is included in the external system controller 20.

The external system controller 20 can in turn be coupled to the batteries 22 or an AC power module 30 that connects to an AC electrical outlet. The external system controller 20 can include a processor 226, a memory device 228 (which can include read-only memory and/or random access-memory), an emergency backup battery (EBB) to power the system (e.g., when the batteries 22 are depleted), one or more display units 230, one or more input/output devices 232, and a communication unit 234, which can have Bluetooth capabilities for wireless data communication. An external computer having a system monitor 32 (which can be operated by a clinician or patient) may further be coupled to the circulatory support system 10 for configuring the external system controller 20, the implanted VAD 14, and/or patient specific parameters; updating software on the external system controller 20 and/or the implanted VAD 14; monitoring system operation; and/or as a conduit for system inputs or outputs.

In some embodiments, the memory device 228 stores one or more software applications that are executable by the processor 226 for various functions. For example, the one or more software applications can effectuate control the motor control unit 222 to effectuate radial levitation and rotational drive of the rotor 140 during operation. In some embodiments, the one or more programs effectuate processing of output from the accelerometer 210 and/or operational parameters for the VAD 14 (e.g., drive current, rotational speed, flow rate, pressure differential across the impeller) as described herein to detect and/or measure patient physiological events and/or activity (e.g., patient orientation, patient activity level, heart wall motion, heart sounds, heart rate, respiratory rate, diaphragm contraction, cardiac cycle timing). The one or more programs can effectuate control of the motor control unit 222 to synchronize variation in output of the VAD 14 with the patient's cardiac cycle timing as described herein. For example, the output of the VAD 14 can be increased over a period of time during ventricular systole so as to augment pumping of blood that occurs via contraction of the ventricle, thereby reducing the associated load on the ventricle. The one or more programs can effectuate control of the motor control unit 222 to vary output of the VAD 14 based on patient activity level. For example, in many embodiments, the output of the VAD 14 is increased in response to increased patient activity and decreased in response to decreased patient activity. The one or more programs can also be used to effectuate processing of the output from the accelerometer 210 and/or the operational parameters for the VAD 14 to generate patient monitoring data and/or VAD monitoring data as described herein. The communication unit 234 provides for wired and/or wireless communication between the external system controller 20 and the VAD 14 and/or the system monitor 32.

Pump Blood Flow Rate During Ventricular Diastole

Figure 8:
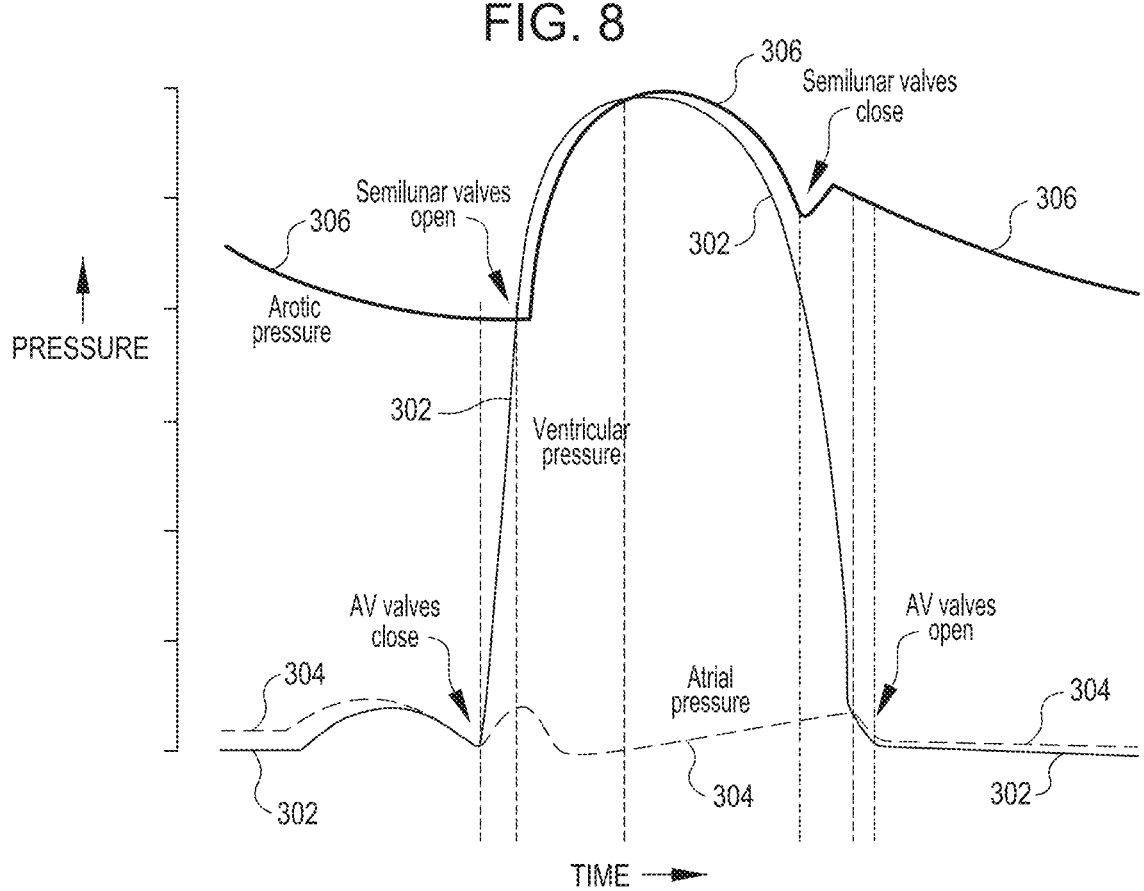
FIG. 8 is a plot of left ventricular pressure, left atrial pressure, and aortic pressure over a cardiac cycle.

FIG. 8 is a plot of left ventricular pressure 302, left atrial pressure 304, and aortic pressure 306 over a cardiac cycle. At the start of the cardiac cycle, the atrioventricular (AV) valves are open and blood flows into the left ventricle and the right ventricle from the left atrium and the right atrium, respectively. During ventricular systole, contraction of the ventricles closes the AV valves and increases the ventricular pressures. During left ventricular systole, the left ventricular pressure 302 increases to a level slightly greater than the aortic pressure 306, thereby causing the native aortic valve to open. Continued contraction of the left ventricle ejects blood from the left ventricle, through the native aortic valve, into the aorta. The ejection of blood into the aorta raises the aortic pressure 306, which is slightly lower that the left ventricular pressure 302 over an initial portion of the blood ejection from the left ventricle and slightly higher than the left ventricular pressure 302 over an end portion of the blood ejection from the left ventricle. At the end of the ejection of blood from the left ventricle to the aorta, the native aortic valve closes in response to the left ventricular pressure 302 being slightly less than the aortic pressure 306. Subsequent relaxation of the left ventricle results in a dramatic reduction of the left ventricular pressure 302 down to a level where the left ventricular pressure 302 is slightly less than the left atrium pressure 304, thereby causing the left AV valve to open.

Figure 9:
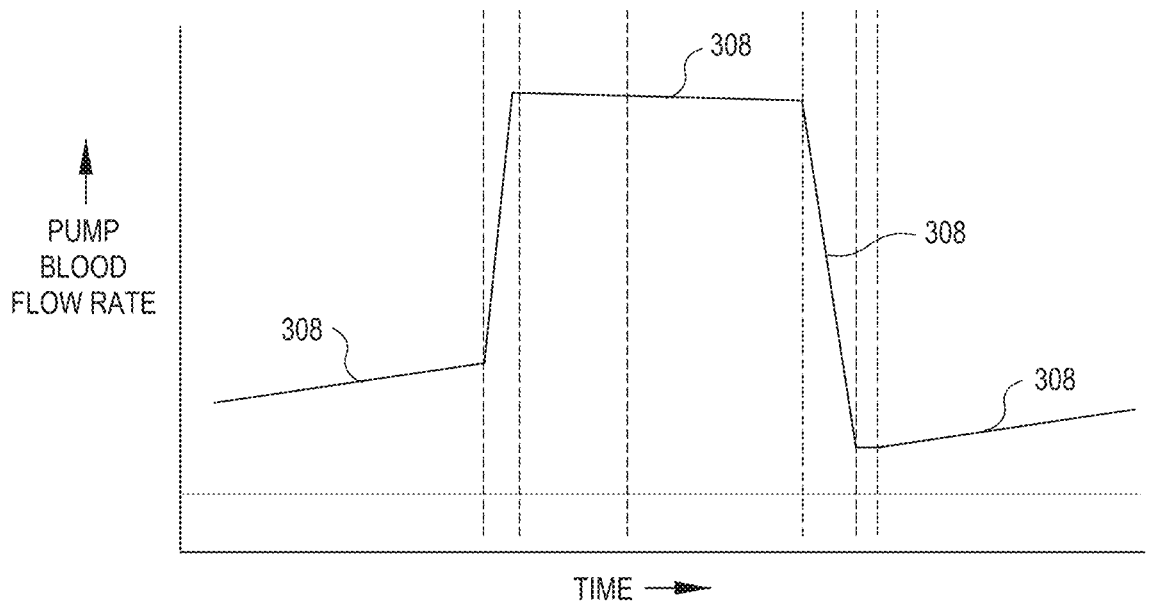
FIG. 9 is a plot of blood flow rate through a blood pump of a left ventricular assist device over a cardiac cycle.

The flow rate of blood through a blood pump of a ventricular assist device typically varies over a cardiac cycle of a patient in response to variation in the pressure differential across the blood pump during the cardiac cycle. For example, FIG. 9 is a plot of an example blood flow rate 308 through a blood pump of a left ventricular assist device over a cardiac cycle of a patient. The illustrated blood flow rate 308 is for a constant rotational speed operation of the blood pump. The blood flow rate 308 in FIG. 9 is aligned with the cardiac cycle of FIG. 8 to better correlate variation in the blood flow rate 308 with pressure differentials illustrated in FIG. 8. At the start of the cardiac cycle, the blood flow rate 308 is relatively low due to the relatively large differential between the aortic pressure 306 and the left ventricular pressure 302. During the initial portion of ventricular systole, the increase in the left ventricular pressure 302 reduces the differential between the aortic pressure 306 and the left ventricular pressure 302, thereby causing a corresponding increase in the blood flow rate 308 due to the decreased pressure differential across the blood pump. During the ejection of blood from the left ventricle into the aorta, the blood flow rate 308 decreases gradually as the aortic pressure 306 gradually increases relative to the left ventricular pressure 302. Following the closure of the native aortic valve, the blood flow rate 308 decreases substantially in response to the increased pressure differential across the blood pump resulting from the decrease in the ventricular pressure 302. Following opening of the AV valves, the blood flow rate 308 gradually increases in response to a gradually decreasing pressure differential across the blood pump resulting primarily from a gradually decrease in the aortic pressure 306.

The rotational speed of a continuous flow blood pump of a VAD is typically limited during ventricular diastole to avoid inducing a suction event in which blood is extracted from the ventricle at an excessive rate. Accordingly, a physician will typically set the rotational speed of the blood pump low enough to ensure that the blood flow rate through the blood pump is low enough to not induce a ventricular suction event.

Figure 10:
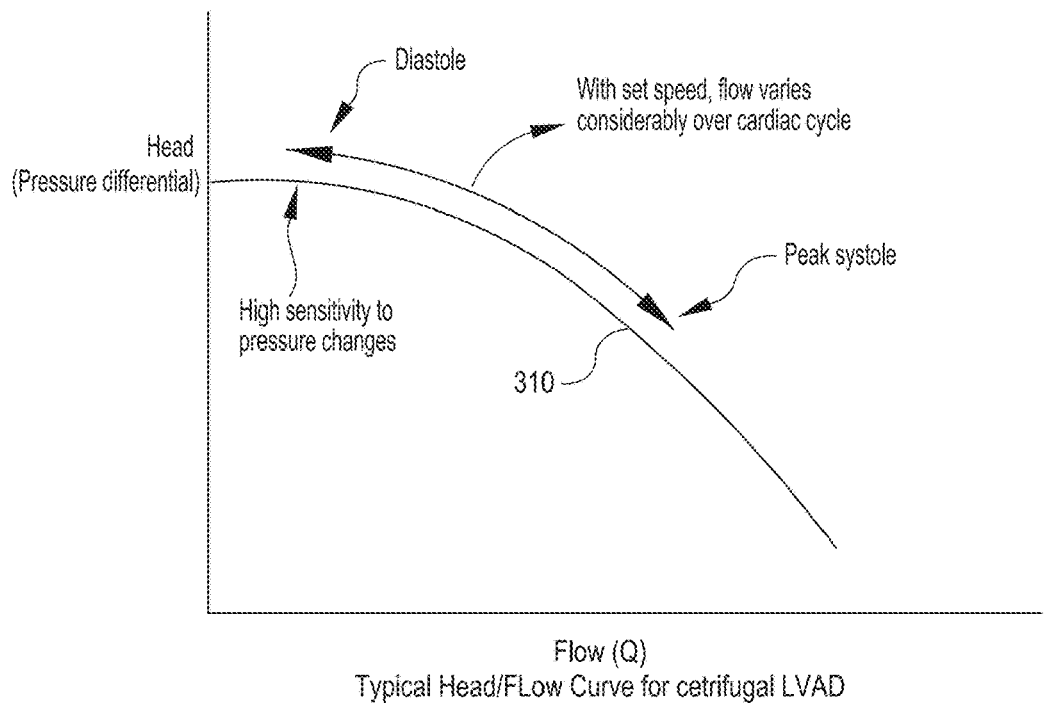
FIG. 10 shows a typical head-flow curve for a centrifugal blood pump.

With the blood flow rate through the blood pump already being low enough to avoid a suction event, any subsequent increase in the patient's blood pressure would further reduce the blood flow rate through the blood pump during ventricular diastole. Continuous flow blood pumps are particularly sensitive to increases in pressure differential across the blood pump at the upper limit of the pressure differential capability of the blood pump. For example, FIG. 10 shows a typical head-flow curve for a centrifugal blood pump operated at a constant rotational speed. At low pressure differential, the flow rate 310 through the blood pump is high. At the upper limit of the pressure differential capability of the blood pump, the flow rate 310 through the blood pump is zero. At low flow rates 310, relatively small changes in pressure differential across the blood pump result in relatively large changes in the flow rate 310. As described herein, when employed in a VAD and operated at constant rotational speed, the speed of the centrifugal blood pump will be set so that the flow rate 310 is low enough during ventricular diastole to avoid inducing a suction event. Operating the centrifugal blood pump at a constant speed selected to produce the relatively low flow rate during ventricular diastole, however, can result in relatively large variation in the flow rate 310 during ventricular diastole in response to relatively small variations in the patient's blood pressure.

Modulating Blood Pump Rotational Speed to Control Pump Flow Rate During Ventricular Diastole Variation in the flow rate 310 during ventricular diastole can result in unsuitable flow rates through the blood pump. For example, a substantial decrease in the patient's blood pressure (relative to the patient's blood pressure corresponding to the set rotational rate of the blood pump during ventricular diastole) may result in an unsuitably high flow rate 310 through the blood pump that induces a suction event. In the other direction, a substantial increase in the patient's blood pressure may result in an unsuitably low flow rate 310 through the blood pump that insufficiently unloads the ventricle prior to ventricular systole. Moreover, especially when the blood pump is operated at a lower rotational speed than normal to provide reduced support during an attempt to wean the patient from the VAD, a substantial increase in the patient's blood pressure may result in retrograde flow through the blood pump, thereby actually adding an unnatural additional burden on the patient's heart during the attempt to wean the patient from the VAD.

Figure 11:
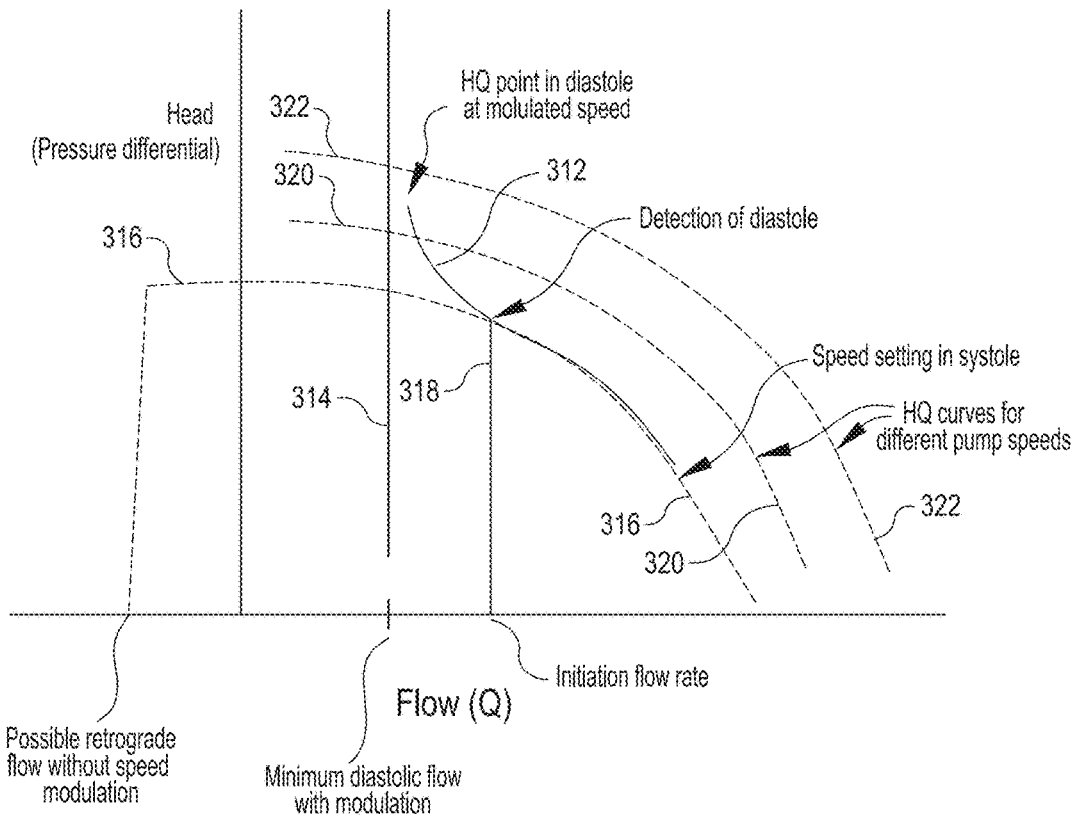
FIG. 11 illustrates modulating rotational speed of a blood pump to prevent flow rate through the blood pump dropping below a target minimum blood flow rate during ventricular diastole, in accordance with embodiments.

In many embodiments, the rotational speed of a blood pump of a VAD is modulated during ventricular diastole to prevent the occurrence of unsuitable flow rates through the blood pump during ventricular diastole. Any suitable approach can be used to monitor the blood flow rate through the blood pump. For example, the blood flow rate through the blood pump can be monitored by estimating the blood flow rate based on drive current supplied to the blood pump, rotational speed of the rotor of the blood pump, blood pressure on the inlet side of the blood pump, and/or blood pressure on the outlet side of the blood pump using known approaches. An inlet side pressure sensor and/or an outlet side pressure sensor can be used to measure the inlet side blood pressure and/or the outlet side blood pressure. The blood flow rate can be estimated based on drive current supplied to the blood pump, rotational speed of the rotor of the blood pump, and the pressure differential across the blood pump. Any suitable approach can be used to estimate or measure the pressure differential across the blood pump. For example, the pressure differential across the blood pump and/or the blood flow rate can be estimate and/or measured as described in U.S. Patent Publication No. 2017-0021070, all of which is incorporated herein by reference for all purposes in its entirety. FIG. 11 illustrates modulating the rotational speed of a blood pump to prevent a flow rate 312 through the blood pump from dropping below a target minimum blood flow rate 314 during ventricular diastole. In the illustrated embodiment, the blood pump is operated at a constant speed 316 during ventricular systole. As the pressure differential across the blood pump increases following closing of the native aortic valve, the flow rate 312 through the blood pump decreases. If the blood pump is operated at the constant speed 316 throughout ventricular diastole, the flow rate 312 may drop below the target minimum blood flow rate 314 if the patient's blood pressure is substantially greater than the patient's blood pressure corresponding to the selection of the constant speed 316. Moreover, especially when the constant speed 316 is selected to provide reduced support to the patient during an attempt to ween the patient from the VAD, the flow rate 312 through the blood pump may even become negative absent modulation of the rotation speed of the blood pump during ventricular diastole. In the illustrated embodiment, the blood flow rate 312 through the blood pump is monitored and the rotation speed of the blood pump is increased when the flow rate 312 has decreased below an initiation flow rate 318 so that the flow rate 312 changes from the initiation flow rate 318 to the target minimum flow rate 314 over a suitable transition period. In the illustrated embodiment, the rotation speed of the blood pump is increased from the constant speed 316, through a rotational speed 320, towards a rotational speed 322. The initiation flow rate 318 can be selected to provide a suitable transition period in view of the rate at which the rotational speed of the blood pump can be increased at a suitable rate. Following the transition period, the rotational speed of the blood pump can then be modulated so that the flow rate 312 through the blood pump is maintained at the target minimum blood flow rate 314 over a suitable portion of ventricular diastole. For example, in some embodiments, the rotational speed of the blood pump is modulated as long as the rotational speed for the flow rate 312 equaling the target minimum blood flow rate 314 is greater than the constant speed 316 at which the blood pump is operated during ventricular systole. In such embodiments, when the rotational speed for the flow rate 312 equaling the target minimum flow rate changes to become less than the constant speed 316, the rotation speed of the blood pump can revert to the constant speed 316.

Figure 12:
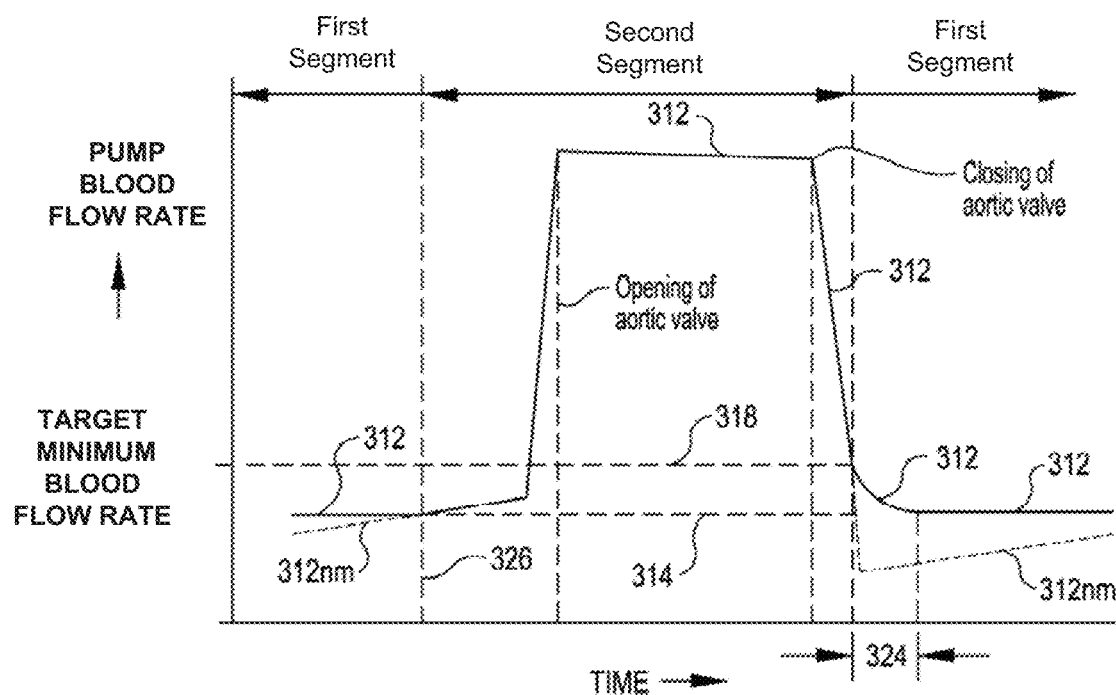
FIG. 12 is a plot of blood flow rate through a blood pump of a left ventricular assist device over a cardiac cycle in which the speed of the blood pump is modulated during ventricular diastole to prevent flow rate through the blood pump dropping below a target minimum blood flow rate, in accordance with embodiments.

FIG. 12 is a plot of the blood flow rate 312 through a blood pump of a left ventricular assist device over a cardiac cycle in which the rotational speed of the blood pump is modulated during ventricular diastole to prevent the flow rate through the blood pump from dropping below a target minimum blood flow rate 314, in accordance with embodiments. The rotational speed of the blood pump is controlled in accordance with a first segment operational mode for the blood pump (e.g., constant speed mode, pulsatile mode, weaning mode) during a first segment of the cardiac cycle and is modulated during ventricular diastole over a second segment of the cardiac cycle to prevent the flow rate through the blood pump from dropping below the target minimum blood flow rate 314. In the illustrated embodiment, the blood flow rate 312 is near maximum during ejection of blood from the left ventricle into the aorta due to the corresponding low pressure differential across the blood pump. Following closure of the native aortic valve, the flow rate 312 decreases in response to the corresponding increase in relative pressure between the left ventricular pressure 302 and the aortic pressure 306. By monitoring the flow rate 312, the rotational speed of the blood pump can be increased starting when the flow rate 312 decreases to an initiation flow rate 318. By increasing the rotational speed of the blood pump, the rate of decrease in the flow rate 312 is reduced to zero over a transition period of time 324. Following the transition period of time 324, the rotation speed of the blood pump is modulated to maintain the flow rate 312 at the target minimum blood flow rate 314 over a suitable portion of the cardiac cycle. In many embodiments, the rotational speed for maintaining the flow rate 312 at the target minimum blood flow rate reduces down to the rotational speed for the blood pump per the first segment operational mode for the blood pump at a reversion point 326. The modulation of the rotational speed of the blood pump can be terminated and the control of the rotational speed of the blood pump can revert to being controlled per the first segment operational mode for the blood pump at the reversion point 326. To illustrate the impact of the modulation of the rotational speed of the blood pump on the flow rate 312 through the blood pump, FIG. 12 shows a flow rate 312nm that would occur if the rotational speed of the blood pump were to be controlled per the first segment operational mode for the blood pump throughout the entire cardiac cycle. The flow rate 312nm increases back up to the target minimum blood flow rate 314 at the reversion point 326.

Figure 13:
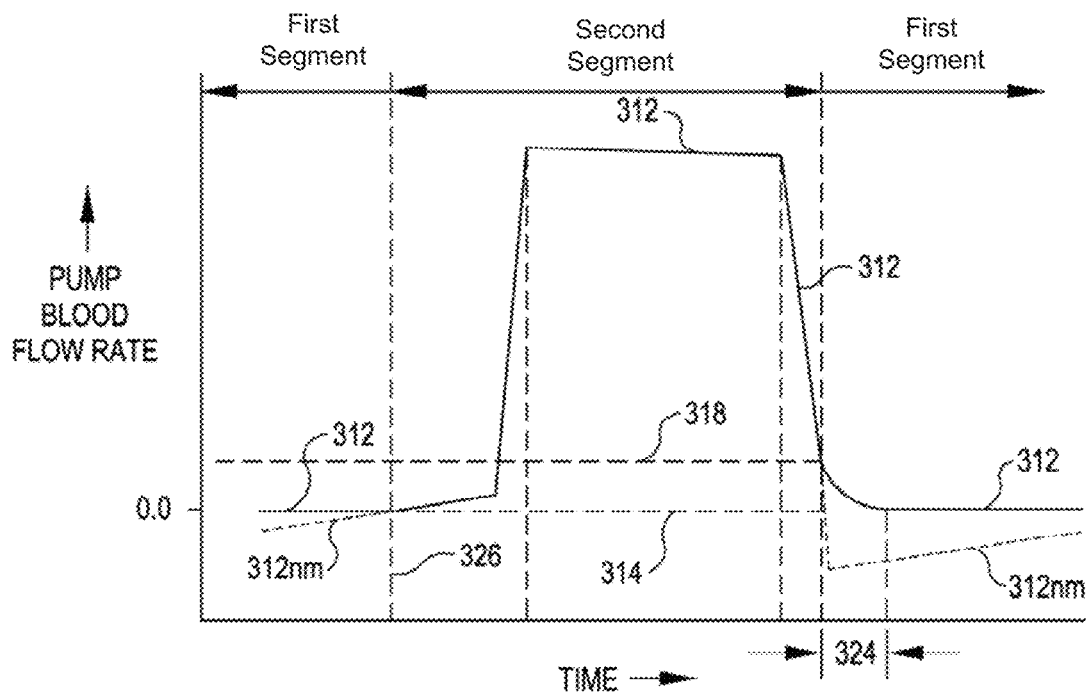
FIG. 13 is a plot of blood flow rate through a blood pump of a left ventricular assist device over a cardiac cycle in which the speed of the blood pump is modulated during ventricular diastole to prevent retrograde flow through the blood pump, in accordance with embodiments.

FIG. 13 is a plot of the blood flow rate 312 through a blood pump of a left ventricular assist device over a cardiac cycle in which the speed of the blood pump is modulated during diastole to prevent retrograde flow through the blood pump, in accordance with embodiments. Over the cardiac cycle shown, the rotational speed of the blood pump is controlled in accordance with a weaning first segment operational mode during the first segment of the cardiac cycle and is modulated during ventricular diastole over a second segment of the cardiac cycle to prevent retrograde flow through the blood pump. The weaning first segment operational mode provides limited circulatory support so as to increase the percentage of the overall blood pumping workload accomplished by the patient's heart. The weaning first segment operational mode can employ any suitable basic first segment operational mode, such as a constant speed mode or a pulsatile mode. In many instances, the rotational speed of the blood pump in the weaning first segment operational mode is lower than for higher support level first segment operational modes and results in the blood flow rate 312 through the blood pump during ventricular diastole being lower than for higher support level first segment operational modes. During the illustrated cardiac cycle, the blood flow rate 312 is near maximum during ejection of blood from the left ventricle into the aorta due to the corresponding low pressure differential across the blood pump. Following closure of the native aortic valve, the flow rate 312 decreases in response to the corresponding increase in relative pressure between the left ventricular pressure 302 and the aortic pressure 306. By monitoring the flow rate 312, the rotational speed of the blood pump can be increased starting when the flow rate 312 decreases to an initiation flow rate 318. By increasing the rotational speed of the blood pump, the rate of decrease in the flow rate 312 is reduced to zero over a transition period of time 324. Following the transition period of time 324, the rotation speed of the blood pump is modulated to maintain the flow rate 312 equal a target minimum blood flow rate during ventricular diastole suitable for weaning the patient from the VAD. In the illustrated embodiment, the rotation speed of the blood pump is modulated so that the flow rate 312 is zero over the second segment of the cardiac cycle. In many embodiments, the rotational speed for maintaining the flow rate 312 at zero reduces down to the rotational speed for the blood pump per the weaning first segment operational mode for the blood pump at a reversion point 326. The modulation of the rotational speed of the blood pump can be terminated and the control of the rotational speed of the blood pump can revert to being controlled per the weaning first segment operational mode for the blood pump at the reversion point 326. To illustrate the impact of the modulation of the rotational speed of the blood pump on the flow rate 312 through the blood pump, FIG. 13 shows a flow rate 312nm (which is retrograde) that would occur if the rotational speed of the blood pump were to be controlled per the weaning first segment operational mode for the blood pump throughout the entire cardiac cycle. The flow rate 312nm increases back up to zero at the reversion point 326.

The initiation flow rate 318 can be determined by adding any suitable initiation flow rate offset to the applicable target minimum blood flow rate 314. For example, a suitable initiation flow rate offset can be selected as a function of the rate at which the blood flow rate 312 is observed to be decreasing following closure of the corresponding semilunar valve. For a faster rate of decline in the blood flow rate 312, a larger initiation flow rate offset can be used to counteract the faster rate of decline in the blood flow rate 312. Likewise, for a slower rate of decline in the blood flow rate 312, a smaller initiation flow rate offset can be used. Suitable initiation flow rate offsets can be stored in memory in a lookup table as a function of the rate at which the blood flow rate 312 is observed to be decreasing. Alternatively, the blood pump can be programmed to determine a suitable modulation of the rotation rate of the blood pump to arrest the observed decline in the blood flow rate 212 to the target blood flow rate. For example, a blood pump can be equipped with machine learning capability to control modulation of the rotational speed of the blood pump to produce a suitable transition from a declining blood flow rate 312 to the target blood flow rate.

Figure 14:
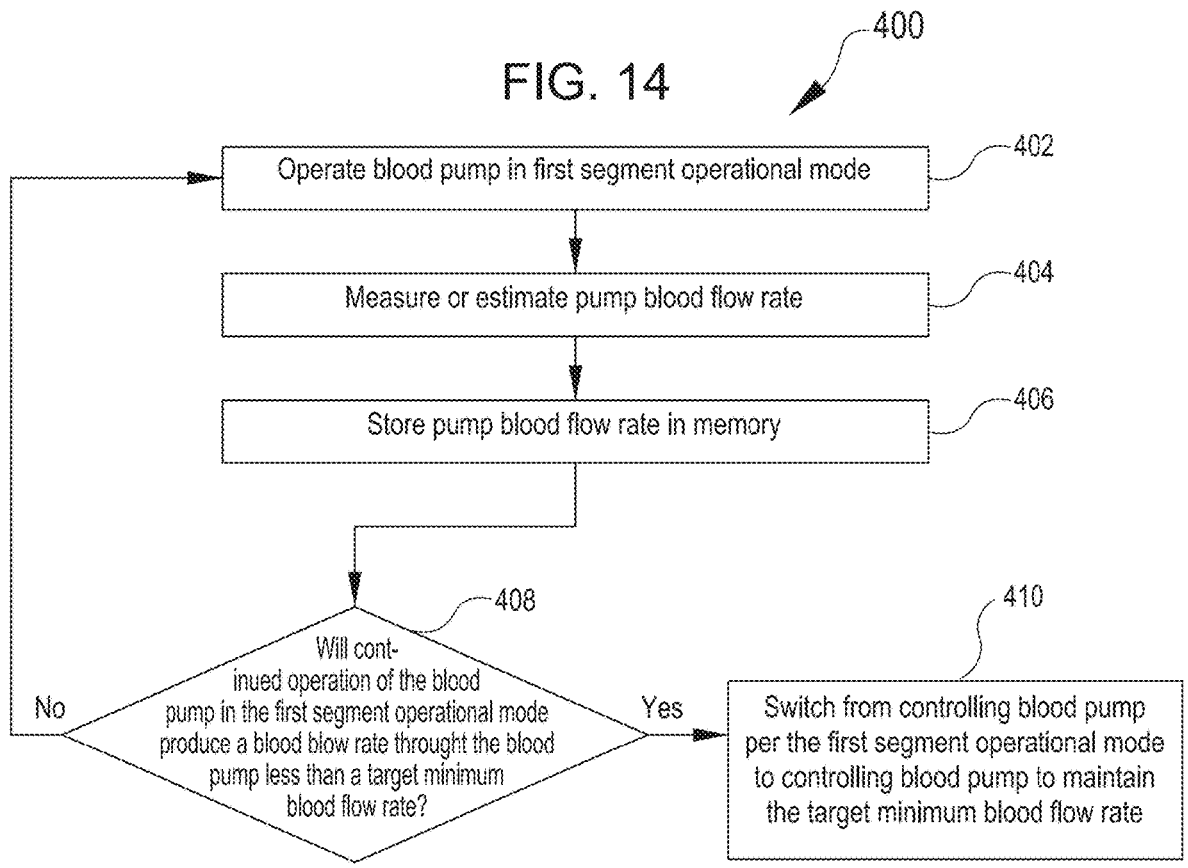
FIG. 14 is a simplified block diagram of a method of operating a blood pump in a first segment operational mode and switching to controlling the blood pump to maintain a target minimum blood flow rate through the blood pump during ventricular diastole, in accordance with embodiments.

FIG. 14 is a simplified block diagram of a method 400 of operating a blood pump in a first segment operational mode over a first segment of a cardiac cycle and switching to controlling the blood pump to maintain a target minimum blood flow rate through the blood pump during ventricular diastole over a second segment of the cardiac cycle, in accordance with embodiments. Any suitable mechanical circulatory assistance system, such as those described herein, can be used to practice the method 400. The method 400 is described herein starting within the first segment of the cardiac cycle. The method includes controlling the rotation rate of the blood pump in the first segment of a cardiac cycle in accordance with the first segment operational mode (act 402). Any suitable first segment operational mode can be used, including, but not limited to, a constant speed mode, a pulsatile mode, and a weaning mode. The method 400 includes measuring or estimating the blood flow rate 312 through the blood pump (act 404). In act 406, the measured or estimated blood flow rate 312 is stored in a memory device, such as in a first in first out buffer, for use in monitoring a rate of change of the blood flow rate 312. In act 408, the current blood flow rate 312 and the current rate of change in the blood flow rate 312 are processed (by a controller) to determine whether continued operation of the blood pump in the first segment operational mode will result in the blood flow rate 312 dropping below a target minimum blood flow rate 314. If continued operation in the first segment operational mode will not result in the blood flow rate 312 dropping below the target minimum blood flow rate 314, the rotation of the blood pump continues to be controlled in accordance with the first segment operational mode and acts 402, 404, 406, 408 are repeatedly accomplished until the controller determines, based on the current blood flow rate 312 and the current rate of change in the blood flow rate 312, that continued operation in the first segment operational mode would result in the blood flow rate 312 dropping below the target minimum blood flow rate 314. For example, where the current blood flow rate 312 is decreasing and the current blood flow rate 312 is at or near the initiation flow rate 318, the controller can switch from controlling the rotation of the blood pump in accordance with the first segment operational mode to controlling the rotation of the blood pump as described herein to cause the blood flow rate 312 to transition to the target minimum blood flow rate 314 and then be maintained at the target minimum blood flow rate 314 for the duration of the second segment (act 410).

Figure 15:
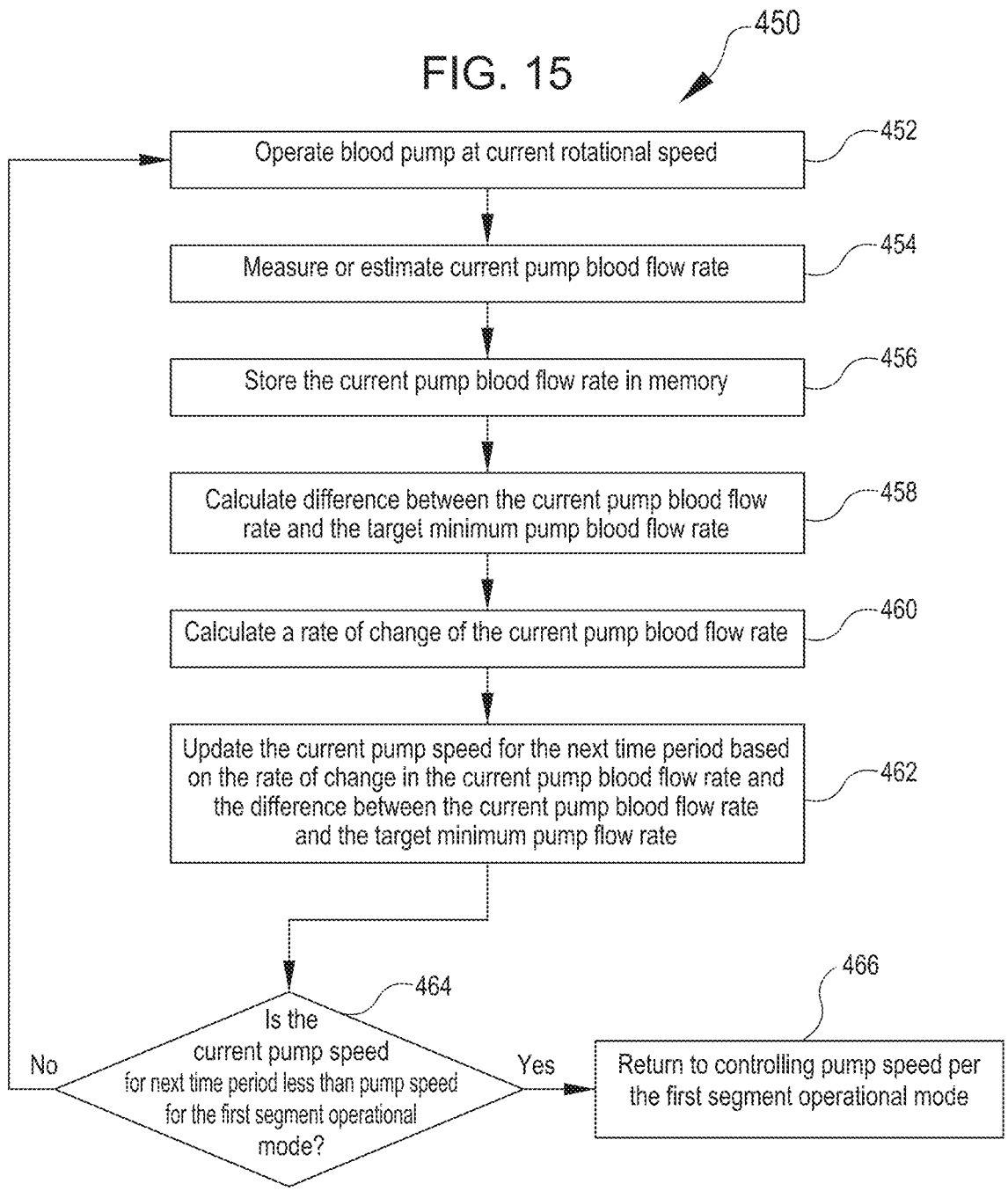
FIG. 15 is a simplified block diagram of a method of controlling a blood pump to maintain a target minimum blood flow rate through the blood pump during ventricular diastole, in accordance with embodiments.

FIG. 15 is a simplified block diagram of a method 450 of controlling the rotation of the blood pump during the second segment of the cardiac cycle, in accordance with embodiments. The method 450 starts by controlling the blood pump to operate at the current rotational speed for the blood pump (act 452). The controller then measures or estimates the current pump blood flow rate 312 (act 454). In act 456, the measured or estimated blood flow rate 312 is stored in a memory device, such as in a first in first out buffer, for use in calculating a rate of change of the current blood flow rate 312. The controller calculates a difference between the current blood flow rate 312 and the target minimum blood flow rate 314 (act 458). The controller also calculates a rate of change of the current blood flow rate 312 (act 460). Based on the calculated difference between the current blood flow rate 312 and the target minimum blood flow rate 314, and the rate of change of the current blood flow rate 312, the controller updates the current rotation rate for the next time period (act 462). For example, a suitable increment to the rotation rate can be stored in a lookup table for each suitable combination of difference between the current blood flow rate 312 and the target minimum blood flow rate 314 and the current rate of change of the current blood flow rate 312 so that when the current rotation rate is updated by the increment for the next time period, the blood flow rate 312 will converge to the target minimum blood flow rate 312 and be maintained at the target minimum blood flow rate 312 thereafter for the remaining duration of the second segment of the cardiac cycle. In act 464, the controller checks whether the current rotation rate for the next time period is less than a rotation rate for the blood pump in accordance with the first segment operational mode. If the current rotation rate for the next time period is less than the rotation rate for the blood pump in accordance with the first segment operational mode, the controller reverts back to controlling the rotation of the blood pump per the first segment operational mode per method 400 (act 466). If the current rotation rate for the next time period is not less than the rotation rate for the blood pump in accordance with the first segment operational mode, acts 452, 454, 456, 458, 462, 464 are repeated until the controller detects the end of the second segment of the cardiac cycle in act 464.

Figure 16:
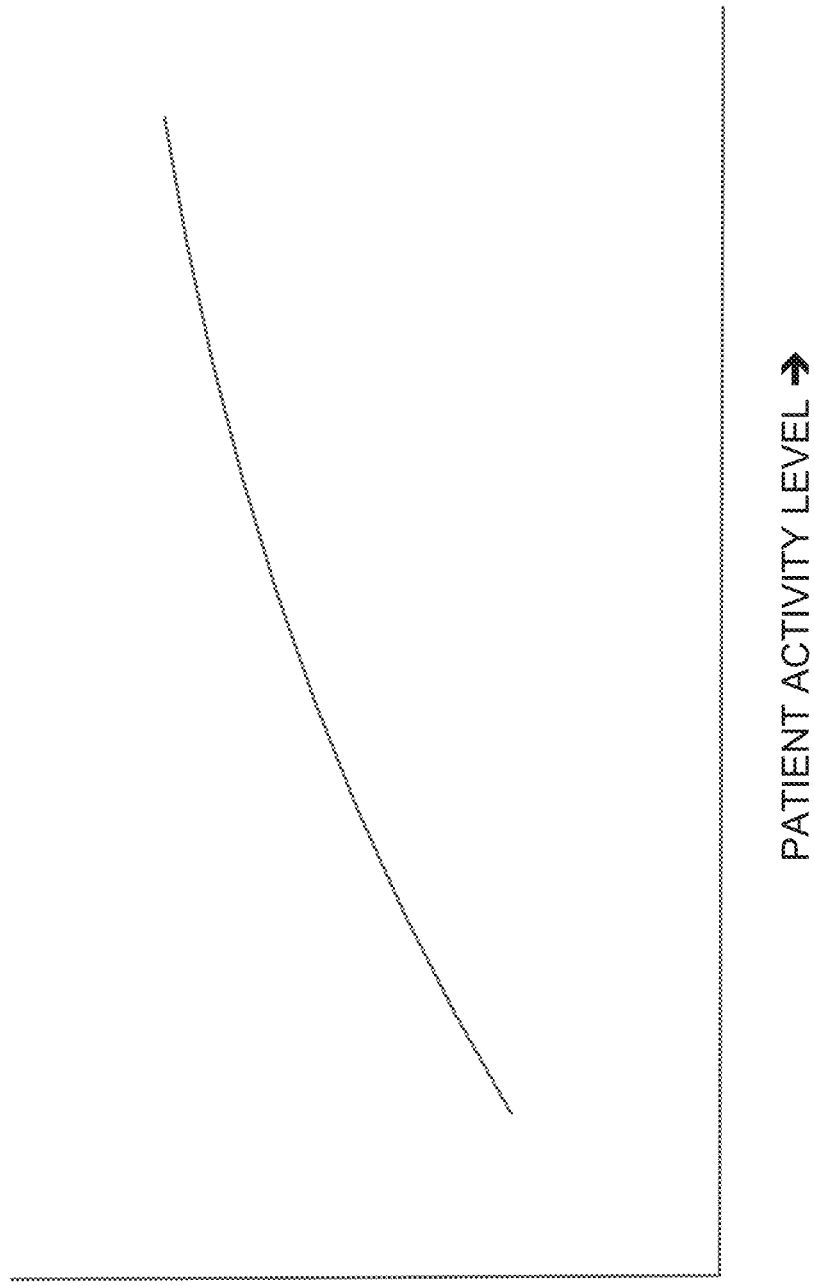
FIG. 16 is a plot showing a variation in a target minimum blood flow rate through a blood pump as a function of patient activity level, in accordance with embodiments.

Any suitable flow rate can be used as the target minimum blood flow rate. For example, as described herein, the target minimum blood flow rate can be any suitable rate within a range from approximately 0 liters/minute to 2.0 liters/minute when the first segment operational mode provides a substantial level of circulatory support to the patient. When the first segment operational mode is a weaning operational mode, the target minimum blood flow rate can be any suitable rate within a range from about 0.0 liters/minute to 0.5 liters/minute. The target minimum blood flow rate can also be selected based on patient activity level. For example, FIG. 16 shows a variation in a target minimum blood flow rate through a blood pump as a function of patient activity level, in accordance with embodiments. The controller can measure the patient activity level using any suitable approach, such as measuring heart rate and/or measuring patient acceleration levels. The measured patient activity level can then be used to select a suitable blood flow rate for the target minimum blood flow rate 314.

Preferred embodiments of this invention are described herein, including the best mode known to the inventors for carrying out the invention. Variations of those preferred embodiments may become apparent to those of ordinary skill in the art upon reading the foregoing description. For example, the target minimum blood flow rate can be a target range of blood flow rates and the rotation rate of the blood flow pump can be modulated during ventricular diastole to maintain the blood flow rate 312 within the target range of blood flow rates. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

What is claimed is:

1. A method of controlling a rotation rate of a blood pump of a ventricular assist device, the method comprising:
    controlling, by a controller, a rotation rate of the blood pump in accordance with a first operational mode to pump blood from a ventricle of a patient to an artery of the patient;
    monitoring, by the controller, a blood flow rate through the blood pump;
    based on the blood flow rate through the blood pump, projecting, by the controller, that the blood flow rate through the blood pump would decrease below a target minimum blood flow rate during a first cardiac cycle ventricular diastole if the rotation rate of the blood pump is controlled in accordance with the first operational mode during the first cardiac cycle ventricular diastole;
    in response to the projection that the blood flow rate through the blood pump would decrease below the target minimum blood flow rate during the first cardiac cycle ventricular diastole, increasing, by the controller, the rotation rate of the blood pump relative to the rotation rate of the blood pump in accordance with the first operational mode to prevent the blood flow rate through the blood pump from dropping below the target minimum blood flow rate;
    based on the blood flow rate through the blood pump, projecting, by the controller, that the blood flow rate through the blood pump would not decrease below a target minimum blood flow rate during a second cardiac cycle ventricular diastole if the rotation rate of the blood pump is controlled in accordance with the first operational mode during the second cardiac cycle ventricular diastole; and
    in response to the projection that the blood flow rate through the blood pump would not decrease below the target minimum blood flow rate during the second cardiac cycle ventricular diastole, continue controlling, by the controller, the rotation rate of the blood pump in accordance with the first operational mode during the second cardiac cycle ventricular diastole.

2. The method of claim 1, wherein the target minimum blood flow rate is within a range from about 0 liters/minute to 2.0 liters/minute.

3. The method of claim 1, wherein the target minimum blood flow rate is within a range from 0.5 liters/minute to 1.5 liters/minute.

4. The method of claim 1, wherein projecting that the blood flow rate through the blood pump would decrease below the target minimum blood flow rate during the first cardiac cycle ventricular diastole comprises determining a relative difference between a current blood flow rate through the blood pump and the target minimum blood flow rate.

5. The method of claim 4, wherein projecting that the blood flow rate through the blood pump would decrease below the target minimum blood flow rate during the first cardiac cycle ventricular diastole comprises determining a current rate of change in the blood flow rate through the blood pump.

6. The method of claim 1, wherein the rotation rate of the blood pump in the first operational mode is constant.

7. The method of claim 1, wherein the rotation rate of the blood pump in the first operational mode is varied to generate a periodic pulsatile blood flow.

8. The method of claim 7, wherein the periodic pulsatile blood flow is synchronized with cardiac cycle timing of the patient.

9. The method of claim 8, wherein the periodic pulsatile blood flow is synchronized with cardiac cycle timing of the patient based on the blood flow rate through the blood pump.

10. The method of claim 8, wherein the rotation rate of the blood pump in accordance with the first operational mode is controlled, by the controller, to generate a blood pressure pulse during ventricular systole.

11. The method of claim 1, further comprising:
detecting, by the controller, when the rotation rate of the blood pump for pumping blood at the target minimum blood flow rate decreases to or below the rotation rate of the blood pump in accordance with the first operational mode of the blood pump; and
in response to detecting when the rotation rate of the blood pump for pumping blood at the target minimum blood flow rate decreases to or below the rotation rate of the blood pump in accordance with the first operational mode of the blood pump, reverting back to controlling the rotation rate of the blood pump in accordance with the first operational mode.

12. The method of claim 1, wherein the rotation rate of the blood pump in the first operational mode results in an opening and a closing of a semilunar valve of the patient during ventricular systole.

13. The method of claim 12, wherein the target minimum blood flow rate is within a range from about 0.0 liters/minute to 0.5 liters/minute.

14. The method of claim 13, wherein the target minimum blood flow rate is 0.0 liters/minute.

15. The method of claim 1, wherein the monitoring of the blood flow rate through the blood pump by the controller comprises estimating the blood flow rate based on the rotation rate of the blood pump and an operational parameter indicative of power consumption by the blood pump.

16. The method of claim 1, wherein the monitoring of the blood flow rate through the blood pump by the controller comprises estimating the blood flow rate based on the rotation rate of the blood pump and an operational parameter indicative of a pressure differential across the blood pump.

17. The method of claim 1, further comprising:
measuring, via a sensor, a patient physiological parameter indicative of an activity level of the patient; and
updating, by the controller, the target minimum blood flow rate based on the patient physiological parameter.

18. The method of claim 17, wherein:
the sensor comprises an accelerometer; and
the patient physiological parameter comprises accelerations of the patient measured by the accelerometer.

19. The method of claim 1, further comprising:
processing one or more operational parameters of the blood pump to measure an activity level of the patient; and
updating, by the controller, the target minimum blood flow rate based on the activity level of the patient.

20. The method of claim 19, wherein the one or more operational parameters of the blood pump comprise a pressure differential across the blood pump.

* * * * *